(12) United States Patent
Oishi

(10) Patent No.: US 8,171,886 B2
(45) Date of Patent: May 8, 2012

(54) STRUCTURE USED IN SEAWATER, COPPER ALLOY WIRE OR BAR FORMING THE STRUCTURE, AND METHOD FOR MANUFACTURING THE COPPER ALLOY WIRE OR BAR

(75) Inventor: Keiichiro Oishi, Yao (JP)

(73) Assignee: Mitsubishi Shindoh Co., Ltd., Tokyo (JP)

( * ) Notice: Subject to any disclaimer, the term of this patent is extended or adjusted under 35 U.S.C. 154(b) by 816 days.

(21) Appl. No.: 10/597,233

(22) PCT Filed: Aug. 10, 2005

(86) PCT No.: PCT/JP2005/014687
§ 371 (c)(1),
(2), (4) Date: Jul. 17, 2006

(87) PCT Pub. No.: WO2006/016621
PCT Pub. Date: Feb. 16, 2006

(65) Prior Publication Data
US 2008/0216759 A1 Sep. 11, 2008

(30) Foreign Application Priority Data
Aug. 10, 2004 (JP) .................. 2004-233952

(51) Int. Cl.
*A01K 61/00* (2006.01)
*C22C 9/02* (2006.01)

(52) U.S. Cl. ........ 119/223; 119/215; 420/471; 420/472; 420/476

(58) Field of Classification Search .................. 119/223; 420/472, 476
See application file for complete search history.

(56) References Cited

U.S. PATENT DOCUMENTS

| 4,047,978 A | * | 9/1977 | Parikh et al. .................. 148/684 |
| 4,110,132 A | | 8/1978 | Parikh et al. |
| 4,710,349 A | | 12/1987 | Yamazaki et al. |
| 4,826,736 A | | 5/1989 | Nakamura et al. |

FOREIGN PATENT DOCUMENTS

| JP | 49-40226 | * | 4/1974 |
| JP | 59-20811 U | | 2/1984 |

(Continued)

OTHER PUBLICATIONS

International Search Report (PCT/ISA/210) Issued in the Corresponding Application PCT/JP2005/014687, Completed Aug. 30, 2005 and Mailed Sep. 13, 2005.

(Continued)

*Primary Examiner* — Jessica L Ward
*Assistant Examiner* — Alexander Polyansky
(74) *Attorney, Agent, or Firm* — Griffin & Szipl, P.C.

(57) ABSTRACT

A fish cultivation net 3 has a rhombically netted form made by arranging a large number of waved wires 6 in parallel such that the adjacent wires are entwined with each other at their curved portions 6a. The wires 6 has a composition containing 62 to 91 mass % of Cu, 0.01 to 4 mass % of Sn, and the balance being Zn. The Cu content [Cu] and the Sn content [Sn] in terms of mass % satisfy the relationship $62 \leq [Cu] - 0.5[Sn] \leq 90$. The copper alloy material has a phase structure including an α phase, a γ phase, and a δ phase and the total area ratio of these phases is 95 to 100%.

113 Claims, 4 Drawing Sheets

FOREIGN PATENT DOCUMENTS

| | | | |
|---|---|---|---|
| JP | 61-048547 A | | 3/1986 |
| JP | 61048547 | * | 3/1986 |
| JP | 07-197150 A | | 8/1995 |
| JP | 10-152735 | * | 6/1998 |
| JP | 10-152735 A | | 6/1998 |
| JP | 10-337132 A | | 12/1998 |
| JP | 11-140677 A | | 5/1999 |
| JP | 2001-164328 A | | 6/2001 |
| JP | 2004-100041 A | | 4/2004 |
| JP | 2004-113003 A | | 4/2004 |

OTHER PUBLICATIONS

Office Action issued in co-pending related U.S. Appl. No. 10/596,849, mailed Oct. 16, 2009.

N.J. Petch, The Cleavage Strength of Polycrystals, Journal of the Iron and Steel Institute, May 1953, pp. 25-28.

E.O. Hall, The Deformation and Ageing of Mild Steel, Mar. 1951, pp. 747-753.

Winfried Reif, Kornfeinung von Aluminium-, Blei-, Zinn-, Kupfer- und Nickellegierungen-ein Überblick, Giesserei 76, 1989, Nr.2, pp. 41-47.

F. Romankiewicz, Kornfeinung von Kupferlegierungen, Metall, 48. Jahrgang, Nr. 11/94, pp. 865-871.

Ferdynand Romankiewicz, Einfluβ einer Kornfeinung mitZirconium auf Erstarrungsmorphologie, Speisungsvermögen und Festigkeitseigenschaften von Messing CuZn30 und Siliciummessing CuZn15S14, 39, Jahrgang 1987 Heft 1, pp. 25-33.

R. Mannheim, Untersuchung der Kornfienung von Kupfer-Zinn-Legierungen mit Zirconium und/oder Bor und Eisen sowie ihres Einflusses auf die mechanischen Eigenschaften, Giessereiforschung 40 1998 Nr. 1, pp. 1-16.

O. Bustos, Estudio de la combinancióón de los procesos de afinamiento de grano de colada y filtrado en latones, Rev. Metal. Madrid, 35 (4), 1999, pp. 222-232.

A. Couture J.O. Edwards, Kornfeinung von Kupfer-Sandguβlegierungen und ihr Einfluβ auf die Güteeigenschaften, Giesserei-Praxis, Nr.21/1974, pp. 425-435.

M. Sadayappan, Fading of Grain Refinement in Leaded Yellow Brass (C85800) and SeBiLOY III (C89550, EnviroBrass III), AFS Transactions 01-116, 2001 American Foundry Society, pp. 705-713.

D. Cousineau, Grain Refinement of Permanent Mold Cast Copper-Base Alloys, AFS Transactions 02-108, 2002 American Foundry Society, pp. 505-514.

J.P. Thomson, Evaluation of Grain Rfinement of Leaded Yellow Brass (C85800) and EnviroBrass III (C89550) using Thermal Analysis, AFS Transactions 2003, pp. 417-434.

F.A. Fasoyinu, Effects of Grain Refinement on Hot Tear Resistance and Shrinkage Characteristics of Permanent Mold Cast Yellow Brass (C85840), pp. 327-337.

M. Sadayappan, Fading of Grain Refinement in Permanent Mold Cast Copper Alloys, AFS Transactions 2004 © American Foundry Society, Des Plaines IL USA, pp. 521-526.

Prof. Dr.-Ing. W. Reif, A New Grain Refiner for Copper-Zinc Alloys containing 25-42%Zinc, Metall 41. Jahrgang Heft Nov. 11, 1987, pp. 1131-1137.

M. Sadayappan, GrainRefinement of Copper Base Alloys, vol. 1—Plenary Lectures/Movement of Copper and Industry Outlook/Copper Applications and Fabrication, 1999, pp. 279-291.

M. Sadayappan, Grain Refinement of Permanent Mold Cast Silicon Brass, Silicon Bronze and Red Brass, AFS Transactions, pp. 337-342.

A. Couture, Grain Refinement of Sand Cast Bronzes and its Influence on Their Properties, AFS Cast Metals Research Journal, Mar. 1974, pp. 1-5.

M. Sadayappan, Grain Refinement Studies on Leaded and Bi/Se Modified Yellow Brasses, pp. 45-58.

M. Sahoo, an Overview of ICA-Funded Research and Development at MTL/Canmet, pp. 1-12.

Metal Handbook Ninth Edition, vol. 9, Metallography and Microstructures, pp. 629-631, filed herewith as Exhibit A.

Metals Handbook Ninth Edition, vol. 9, Metallography and Microstructures (American Society for Metals), pp. 641-642, filed herewith as Exhibit B.

pp. 290 & C-2 of Metals Handbook 8th Edition, vol. 7, Atlas of Microstructures of Industrial Alloys (American Society for Metals), filed herewith as Exhibit C.

p. 286 of Metals Handbook 8th Edition, vol. 7, Atlas of Microstructures of Industrial Alloys (American Society for Metals), filed herewith as Exhibit D.

Office Action dated Jan. 20, 2010 in co-pending related U.S. Appl. No. 10/597,454, filed Jan. 30, 2007.

The English Translation of JP 61-048547 provided by the USPTO, filed herewith as "Exhibit A1."

Metals and Corrosion Resistance, downloaded from http://www.engineeringtoolbox.com/metal-corrosion-resistance-..., on Jan. 14, 2011, 4 pages, filed herewith as "Exhibit A2".

Fundamentals of Corrosion and Corrosion control, downloaded from http://corrosion.ksc.nasa.gove/corr_fundamentals.htm, on Jan. 14, 2011, 2 pages, filed herewith as "Exhibit A3".

Why Metals Corrode, downloaded from http://corrosion.ksc.nasa.gove/corr_metal.htm, on Jan. 14, 2011, 2 pages, filed herewith as "Exhibit A3".

Forms of Corrosion, http://corrosion.ksc.nasa.gove/corr_forms.htm, on Jan. 14, 2011, 3 pages), filed herewith as "Exhibit A3".

Eight Forms of Corrosion, downloaded from http://corrosion-doctors.org/Corrosion-History/Eight.htm, on Jan. 14, 2011, 4 pages, filed herewith as "Exhibit A4".

* cited by examiner though it has been proposed that a cultivation net
STRUCTURE USED IN SEAWATER, COPPER ALLOY WIRE OR BAR FORMING THE STRUCTURE, AND METHOD FOR MANUFACTURING THE COPPER ALLOY WIRE OR BAR This is a National Phase Application in the United States of International Patent Application No. PCT/JP2005/14687 filed Aug. 10, 2005, which claims priority on Japan Patent Application No. 2004-233952, filed Aug. 10, 2004. The entire disclosures of the above patent applications are hereby incorporated by reference.

TECHNICAL FIELD

The present invention relates to seawater netted structures used under or in contact with seawater, such as fish cultivation nets, seawater intakes of power generating installations or desalinating installations, and seawater strainers of marine engines, to a copper alloy wire or bar used for the netted structure, and to a method for manufacturing the copper alloy wire or bar.

BACKGROUND ART

For example, cultivation nets used for culturing fish, such as tuna, yellowtail, or globefish, are generally made of iron or artificial fiber, such as nylon, polypropylene, or polyethylene (for example, Patent Document 1).

Unfortunately, iron cultivation nets (hereinafter referred to as iron nets) and artificial fiber cultivation nets (hereinafter referred to as synthetic nets) easily trap marine organisms, such as ("acorn shells") and other shellfishes and algae. The marine organisms clog the mesh of the net and thus make it difficult for seawater to pass through the mesh. Consequently, oxygen and nutrients in water cannot be sufficiently supplied to cultivation regions, and thus cultured fish become anorectic. Thus, the productivity and physical strength of the cultured fish are reduced. The cultivation yield is reduced as the resistance to pathogenic bacteria is weakened. Also, parasites, such as gill worms and skin worms, are easily produced. The marine organisms adhering to the net interfere with the behavior of tuna and other migratory fish rubbing against the net. This can adversely affect the growth of cultured fish due to stresses and diseases. Accordingly, it is necessary to frequently remove trapped marine organisms from the net and parasites from the cultured fish. Such work is hard and harsh, and requires extremely high costs.

Furthermore, the iron net is liable to be broken in a relatively short time by corrosion of its wires, because iron being the constituent material of the net has a low corrosion resistance to seawater. Even if only a part of a net is broken, cultured fish can escape from the breakage and this results in considerable losses. The iron net therefore needs to be replaced at regular intervals. The iron net is generally replaced about every two years (or about every year, in some cases). The lifetime of the iron net is thus very short. On the other hand, the synthetic net more easily traps marine organisms, such as shellfishes and algae, than the iron net, and it is accordingly necessary to remove the trapped marine organisms with a frequency of more than or equal to that of the iron net. Although the synthetic net is not corroded by seawater, it inherently has a low shearing strength. Some synthetic nets may result in a shorter lifetime than the iron net depending on circumstances, and may need to be replaced in a shorter time. For replacing a net, cultured fish must be transferred. The replacement of the net not only requires much effort and cost, but also produces adverse effects (for example, stresses) on the cultured fish. The synthetic net also needs to be coated with an antifoulant on a regular basis. The efforts and costs for this work are also high, and the cost for disposing of the waste antifoulant cannot be ignored.

Accordingly, it has been proposed that a cultivation net made of copper alloy wires (hereinafter referred to as the copper net) be used instead of the iron net or synthetic net having the above-described disadvantages (for example, Patent Document 2). In use of the copper net, Cu ions leaching from the wires prevent marine organisms, such as ("acorn shells"), from adhering to the net (this is referred to as "antifouling property") and sterilize or disinfect the culturing seawater region. Hence, it is not necessary to remove organisms adhering to the net. Accordingly, the efforts and costs for removing organisms can be reduced while adverse effects on cultured fish are eliminated. Furthermore, the sterilization or disinfection of culturing regions can prevent diseases of cultured fish and adverse effects of parasites as much as possible, thus allowing the cultured fish to grow healthily at a high speed.

Patent Document 1: Japanese Unexamined Patent Application Publication No. 10-337132
Patent Document 2: Japanese Unexamined Patent Application Publication No. 11-140677

DISCLOSURE OF INVENTION

Problems to be Solved by the Invention

Cultivation nets are hung under the surface of the sea. If the mechanical strength of the wires of a net is insufficient, the wires may be broken due to their own weight. The cultivation net is swung by waves and wind and rubbed by behaviors of migratory fish. Consequently, the wires are brought into strong contact (rubbed) with each other and finally worn out. In addition, the cultivation net undergoes repeated collisions with waves. The impacts by the collisions erode the wires of the nets, thereby making the wires thin (so-called erosion-corrosion phenomenon). Furthermore, seawater corrodes metal. The wires are corroded by contact with seawater (this is hereinafter referred to as "seawater corrosion"). At the water line, the rate of seawater corrosion is increased by an oxygen concentration cell or other electrochemical reaction. Therefore, a cultivation net made of wires in which any one of the mechanical strength, the wear resistance, the erosion-corrosion resistance, and the seawater corrosion resistance is insufficient has an unsatisfactory lifetime.

Although various materials for copper nets have been proposed, known copper alloys do not satisfy all the requirements for the cultivation net in terms of the mechanical strength, the wear resistance, the erosion-corrosion resistance, and the seawater corrosion resistance. For example, pure copper-based alloys have problems with strength, wear resistance, and erosion-corrosion resistance; Cu—Zn copper alloys have problems with wear resistance, erosion-corrosion resistance, and seawater corrosion resistance including dezincification corrosion resistance; Cu—Ni copper alloys have problems with wear resistance and erosion-corrosion resistance (and besides material costs). According to experimental results obtained by the present inventors, cultivation nets made of known copper alloys have lifetimes shorter than or equal to those of iron nets. For example, even a net made of naval bronze (JIS C4621, CDA C46400, C46500), which is a copper alloy having a superior seawater resistance, has only substantially the same lifetime as iron nets (lifetime of at most about two years). Since the cultivation net made of a copper alloy uses more expensive material than the iron or synthetic net, the copper net having such a lifetime is money-losing even though it is advantageous in antifouling and disinfection and sterilization. The copper net has not been yet put into practical use because of its poor total cost efficiency including lifetime, although it has an antifouling, a bactericidal, and a sterilizing property superior in cultivation to iron nets and synthetic nets.

Accordingly, the object of the present invention is to provide a netted structure used in seawater, such as a fish cultivation net, which has a highly enhanced durability including seawater resistance, with its inherent properties maintained, and to provide a Cu—Zn—Sn copper alloy material in wire or bar form suitably used for the netted structure.

Means for Solving the Problems

According to a first aspect of the present invention, a Cu—Zn—Sn copper alloy material in wire or bar form is provided which forms a seawater netted structure intended for use under or in contact with seawater, such as a fish cultivation net. The copper alloy material is selected from among the following first to sixth compositions.

A first copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; and the balance being Zn. The compositional value Y1=[Cu]−0.5[Sn] derived from the Cu content [Cu] and Sn content [Sn] in terms of mass % is 62 to 90 (preferably 62.5 to 81, more preferably 63 to 76, most preferably 64 to 74). The copper apply material has a phase structure including an α phase, a γ phase, and a δ phase, and the total area ratio of the α, γ, and δ phases is 95 to 100% (preferably 98 to 100%, more preferably 99.5 to 100%).

A second copper alloy material further contains at least one element X1 selected from the group consisting of As, Sb, Mg, and P, in addition to the composition of the first copper alloy material. More specifically, the second copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; at least one element X1 selected from the group consisting of 0.02 to 0.25 mass % (preferably 0.03 to 0.12 mass %) of As, 0.02 to 0.25 mass % (preferably 0.03 to 0.12 mass %) of Sb, 0.001 to 0.2 mass % (preferably 0.002 to 0.15 mass %, more preferably 0.005 to 0.1 mass %) of Mg, and 0.01 to 0.25 mass % (preferably 0.02 to 0.18 mass %, more preferably 0.025 to 0.15 mass %, most preferably 0.035 to 0.12 mass %) of P; and the balance being Zn. The compositional value Y2=[Cu]−0.5[Sn]−3[P]−0.5[X0] derived from the Cu content [Cu], Sn content [Sn], P content [P], and X1 total content [X1] (except P) in terms of mass % is 62 to 90 (preferably 62.5 to 81, more preferably 63 to 76, most preferably 64 to 74). The copper alloy material has a phase structure including an α phase, a γ phase, and a δ phase, and the total area ratio of the α, γ, and δ phases is 95 to 100% (preferably 98 to 100%, more preferably 99.5 to 100%).

A third copper alloy material further contains at least one element X2 selected from the group consisting of Al, Mn, Si, and Ni, in addition to the composition of the first copper alloy material. More specifically, the third copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; at least one element X2 selected from the group consisting of 0.02 to 1.5 mass % (preferably 0.05 to 1.2 mass %, more preferably 0.1 to 1 mass %) of Al, 0.05 to 1.5 mass % (preferably 0.2 to 1 mass %) of Mn, 0.02 to 1.9 mass % (preferably 0.1 to 1 mass %) of Si, and 0.005 to 0.5 mass % (preferably 0.005 to 0.1 mass %) of Ni; and the balance being Zn. The compositional value Y3=[Cu]−0.5[Sn]−3.5[Si]−1.8 [Al]+[Mn]+[Ni] derived from the Cu content [Cu], Sn content [Sn], Al content [Al], Mn content [Mn], Si content [Si], and Ni content [Ni] in terms of mass % is 62 to 90 (preferably 62.5 to 81, more preferably 63 to 76, most preferably 64 to 74). The copper alloy material has a phase structure including an α phase, a γ phase, and a δ phase, and the total area ratio of the α, γ, and δ phases is 95 to 100% (preferably 98 to 100%, more preferably 99.5 to 100%).

A fourth copper alloy material further contains the elements X1 and X2 in addition to the composition of the first copper alloy material. More specifically, the fourth copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; at least one element X1 selected from the group consisting of 0.02 to 0.25 mass % (preferably 0.03 to 0.12 mass %) of As, 0.02 to 0.25 mass % (preferably 0.03 to 0.12 mass %) of Sb, 0.001 to 0.2 mass % (preferably 0.002 to 0.15 mass %, more preferably 0.005 to 0.1 mass %) of Mg, and 0.01 to 0.25 mass % (preferably 0.02 to 0.18 mass %, more preferably 0.025 to 0.15 mass %, most preferably 0.035 to 0.12 mass %) of P; at least one element X2 selected from the group consisting of 0.02 to 1.5 mass % (preferably 0.05 to 1.2 mass %, more preferably 0.1 to 1 mass %) of Al, 0.05 to 1.5 mass % (preferably 0.2 to 1 mass %) of Mn, 0.02 to 1.9 mass % (preferably 0.1 to 1 mass %) of Si, and 0.005 to 0.5 mass % (preferably 0.005 to 0.1 mass %) of Ni; and the balance being Zn. The compositional value Y4=[Cu]−0.5[Sn]−3[P]−0.5[X1]−3.5[Si]−1.8 [Al]+[Mn]+[Ni] derived from the Cu content [Cu], Sn content [Sn], P content [P], total X1 content [X1] (except P), Al content [Al], Mn content [Mn], Si content [Si], and Ni content [Ni] is 62 to 90 (preferably 62.5 to 81, more preferably 63 to 76, most preferably 64 to 74). The copper alloy material has a phase structure including an α phase, a γ phase, and a δ phase, and the total area ratio of the α, γ, and δ phases is 95 to 100% (preferably 98 to 100%, more preferably 99.5 to 100%).

Preferably, the total area ratio of the γ and δ phases in the first to fourth copper alloy materials is 0 to 10% (more preferably 0 to 5%, still more preferably 0 to 3%).

A fifth copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; 0.0008 to 0.045 mass % (preferably 0.002 to 0.029 mass %, more preferably 0.004 to 0.024 mass %, most preferably 0.006 to 0.019 mass %) of Zr; 0.01 to 0.25 mass % (preferably 0.02 to 0.18 mass %, more preferably 0.025 to 0.15 mass %, most preferably 0.035 to 0.12 mass %) of P; and the balance being Zn. The compositional value Y5=[Cu]−0.5[Sn]−3[P] derived from the Cu content [Cu], Sn content [Sn], and P content [P] in terms of mass % is 62 to 90 (preferably 62.5 to 81, more preferably 63 to 76, most preferably 64 to 74). The copper alloy material has a phase structure including an α phase, a γ phase, and a δ phase, and the total area ratio of the α, γ, and δ phases is 95 to 100% (preferably 98 to 100%, more preferably 99.5 to 100%). Also, the average grain size of the copper alloy material is 0.2 mm or less (preferably 0.1 mm or less, optimally 0.06 mm or less)

after melt-solidification. The average grain size after melt-solidification mentioned in the fifth copper alloy material and the below-described sixth to eighth copper alloy materials refers to the average of macroscopic and/or microscopic crystal grain sizes after melt-solidification performed by casting or welding the copper alloy material, without deformation processing (extrusion, rolling, etc.) or heat treatment.

A sixth copper alloy material further contains at least one element X3 selected from the group consisting of As, Sb, and Mg, in addition to the composition of the fifth copper alloy material. More specifically, the sixth copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; 0.0008 to 0.045 mass % (preferably 0.002 to 0.029 mass %, more preferably 0.004 to 0.024 mass %, most preferably 0.006 to 0.019 mass %) of Zr; 0.01 to 0.25 mass % (preferably 0.02 to 0.18 mass %, more preferably 0.025 to 0.15 mass %, most preferably 0.035 to 0.12 mass %) of P; at least one element X3 selected from the group consisting of 0.02 to 0.25 mass % (preferably 0.03 to 0.12 mass %) of AS, 0.02 to 0.25 mass % (preferably 0.03 to 0.12 mass %) of Sb, and 0.001 to 0.2 mass % (preferably 0.002 to 0.15 mass %, more preferably 0.005 to 0.1 mass %) of Mg; and the balance being Zn. The compositional value $Y6=[Cu]-0.5[Sn]-3[P]-0.5[X3]$ derived from the Cu content [Cu], Sn content [Sn], P content [P], and total X3 content [X3] in terms of mass % is 62 to 90 (preferably 62.5 to 81, more preferably 63 to 76, most preferably 64 to 74). The copper alloy material has a phase structure including an α phase, a γ phase, and a δ phase, and the total area ratio of the α, γ, and δ phases is 95 to 100% (preferably 98 to 100%, more preferably 99.5 to 100%). The average grain size after melt-solidification is 0.2 mm or less (preferably 0.1 mm or less, most preferably 0.06 mm or less).

A seventh copper alloy material further contains at least one element X4 selected from the group consisting of Al, Mn, Si, and Ni in addition to the composition of the fifth copper alloy material. More specifically, the seventh copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; 0.0008 to 0.045 mass % (preferably 0.002 to 0.029 mass %, more preferably 0.004 to 0.024 mass %, most preferably 0.006 to 0.019 mass %) of Zr; 0.01 to 0.25 mass % (preferably 0.02 to 0.18 mass %, more preferably 0.025 to 0.15 mass %, most preferably 0.035 to 0.12 mass %) of P; at least one element X4 selected from the group consisting of 0.02 to 1.5 mass % (preferably 0.05 to 1.2 mass %, more preferably 0.1 to 1 mass %) of Al, 0.05 to 1.5 mass % (preferably 0.2 to 1 mass %) of Mn, 0.02 to 1.9 mass % (preferably 0.1 to 1 mass %) of Si, and 0.005 to 0.5 mass % (preferably 0.005 to 0.1 mass %) of Ni; and the balance being Zn. The compositional value $Y7=[Cu]-0.5[Sn]-3[P]-3.5[Si]-1.8[Al]+[Mn]+[Ni]$ derived from the Cu content [Cu], Sn content [Sn], P content [P], Al content [Al], Mn content [Mn], Si content [Si], and Ni content [Ni] in terms of mass % is 62 to 90 (preferably 62.5 to 81, more preferably 63 to 76, most preferably 64 to 74). The copper alloy material has a phase structure including an α phase, a γ phase, and a δ phase, and the total area ratio of the α, γ, and δ phases is 95 to 100% (preferably 98 to 100%, more preferably 99.5 to 100%). Also, the average grain size after melt-solidification is 0.2 mm or less (preferably 0.1 mm or less, most preferably 0.06 mm or less).

A eighth copper alloy material further contains the elements X3 and X4 in addition to the composition of the fifth copper alloy material. More specifically, the eighth copper alloy material has a composition containing: 62 to 91 mass % (preferably 63 to 82 mass %, more preferably 64 to 77 mass %) of Cu; 0.01 to 4 mass % (preferably 0.1 to 3 mass %, more preferably 0.6 to 3 mass %, most preferably 0.8 to 2.5 mass %) of Sn; 0.0008 to 0.045 mass % (preferably 0.002 to 0.029 mass %, more preferably 0.004 to 0.024 mass %, most preferably 0.006 to 0.019 mass %) of Zr; 0.01 to 0.25 mass % (preferably 0.02 to 0.18 mass %, more preferably 0.025 to 0.15 mass %, optimally 0.035 to 0.12 mass %) of P; at least one element X3 selected from the group consisting of 0.02 to 0.25 mass % (preferably 0.03 to 0.12 mass %) of As, 0.02 to 0.25 mass % (preferably 0.03 to 0.12 mass %) of Sb, 0.001 to 0.2 mass % (preferably 0.002 to 0.15 mass %, and more preferably 0.005 to 0.1 mass %) of Mg; at least one element X4 selected from the group consisting of 0.02 to 1.5 mass % (preferably 0.05 to 1.2 mass %, more preferably 0.1 to 1 mass %) of Al, 0.05 to 1.5 mass % (preferably 0.2 to 1 mass %) of Mn, 0.02 to 1.9 mass % (preferably 0.1 to 1 mass %) of Si, and 0.005 to 0.5 mass % (preferably 0.005 to 0.1 mass %) of Ni; and the balance being Zn. The compositional value $Y8=[Cu]-0.5[Sn]-3[P]-0.5[X3]-3.5[Si]-1.8[Al]+[Mn]+[Ni]$ derived from the Cu content [Cu], Sn content [Sn], P content [P], total X3 content [X3], Al content [Al], Mn content [Mn], Si content [Si], and Ni content [Ni] in terms of mass % is 62 to 90 (preferably 62.5 to 81, more preferably 63 to 76, most preferably 64 to 74). The copper alloy material has a phase structure including an α phase, a γ phase, and a δ phase, and the total area ratio of the α, γ, and δ phases is 95 to 100% (preferably 98 to 100%, more preferably 99.5 to 100%). Also, the average grain size after melt-solidification is 0.2 mm or less (preferably 0.1 mm or less, most preferably 0.06 mm or less).

Each of the fifth to eighth copper alloy materials is prepared by adding Zr and P, which are grain-refining elements, to each composition of the first to fourth copper alloy materials. Thus, the crystal grains of the fifth to eighth copper alloy materials are refined after melt-solidification so as to further improve the characteristics that the first to fourth copper alloy materials originally have and so as to ensure a high castability. Specifically, the fifth to eighth copper alloy materials respectively have the same or substantially the same composition (constituted of the same elements in the same proportions except the balance being Zn) as the first to fourth copper alloy materials (referred to as copper alloy materials before improvement for the comparison with the fifth to eighth copper alloy materials), except for containing Zr and P. Each of the fifth to eighth copper alloy materials is modified so that its macroscopic or microscopic average grain size is reduced by ¼ or less (preferably ⅒ or less, more preferably ¹⁄₂₅ or less) after melt-solidification, by adding Zr and P together. In order to modify the cooper alloy material more effectively, the Sn content [Sn], Zr content [Zr], and P content [P] in terms of mass % of the fifth to eighth copper alloy materials preferably satisfy $Z1=0.5$ to 150 (preferably $Z1=0.8$ to 50, more preferably $Z1=1.5$ to 15, most preferably $Z1=2.0$ to 12), $Z2=1$ to 3000 (preferably $Z2=15$ to 1000, more preferably $Z2=30$ to 500, most preferably $Z2=40$ to 300), and $Z3=0.2$ to 250 (preferably $Z3=3$ to 160, more preferably $Z3=5$ to 90, most preferably $Z3=8$ to 60), wherein $Z1=[P]/[Zr]$, $Z2=[Sn]/[Zr]$, and $Z3=[Sn]/[P]$. In addition, the total area ratio of the γ and δ phases in the phase structure is preferably 0 to 10% (more preferably 0 to 5%, still more preferably 0 to 3%). Optimally, the γ phase is in a boundary state where it may be formed or not; hence, it is most preferable that the area ratio of the γ phase be enormously close to 0%. Optimally, the β phase is not produced, or if produced, its area ratio should be limited to 5% or less. Preferably, the fifth to eighth copper alloy materials each result in a crystal structure whose dendritic network is broken after melt-solidification, and more preferably the two-dimensional crystal grain structure is in a circular form or a similar form after melt-solidification. In order to refine the crystal grains during melt-solidification, it is important to take into account the cooling speed during melt-solidification. For example, if the cooling speed is 0.05° C./s or less, the rate of dendrite growth becomes higher than that of crystal nucleation, so that the crystal nucleation is canceled by the dendrite growth. Consequently, the crystal grains cannot be refined effectively. In order to produce fine circular or similar crystal grains, it is preferable that the cooling speed during melt-solidification be taken into account. In general, a preferred cooling speed is 0.1° C./s or more (more preferably 0.3° C./s or more). The crystal grain size, crystal structure, and two-dimensional crystal grain structure after melt-solidification refer to those after melt-solidification performed by casting or welding the fifth to eighth copper alloy materials, without deformation processing, such as extrusion or rolling, or heat treatment.

Any of the fifth to eighth copper alloy materials may contain inevitable impurities. If the copper alloy material contains Fe and/or Ni as inevitable impurities (except for the seventh and eighth copper alloy materials containing Ni), their contents are each preferably 0.5 mass % or less. If the content of these impurities is high, they consume Zr and P (which contribute to crystal grain refining), to inhibit the crystal grain refining, disadvantageously. It is therefore preferable that if Fe and/or Ni is contained as impurities, their contents are each limited to 0.5 mass % or less (more preferably 0.2 mass % or less, still more preferably 0.1 mass % or less, most preferably 0.05 mass % or less).

The first to fourth copper alloy materials are generally provided in plastic-processed form prepared by plastic processing (extrusion or rolling, and physical deformation processing that may be performed subsequent to the extrusion or rolling, such as wiredrawing, drawing, or rolling) in which large casting material (for example, billet or ingot) obtained by metal mold casting is formed into wires or bars. For example, such plastic-processed materials include primary plastic-processed wires or bars obtained by extruding or rolling a casting material and secondary plastic-processed wires or bars obtained by subjecting the primary plastic-processed wires or bars to wiredrawing, drawing, or rolling. The fifth to eighth copper alloy materials are provided in combined-processed wire or bar form prepared by casting, such as horizontal continuous casting or upward casting (up-casting), or by subsequently subjecting the cast-processed material to plastic processing (physical deformation processing, such as wiredrawing). The combined-processed material is obtained by, for example, wiredrawing, drawing, or rolling of a cast-processed material. In the plastic processing for preparing the plastic-processed material or the combined-processed material, the following cases can be thought of according to the difference between the diameters before and after processing the wires or bars: (1) the same procedure for plastic processing is repeated several times (for example, wiredrawing or drawing is repeated several times); (2) different types of plastic processing are combined (for example, a material is extruded, and subsequently the extruded material is subjected to wiredrawing), and (3) cases (1) and (2) are combined (for example, an extruded material is repeatedly subjected to wiredrawing several times). In any case of (1) to (3), appropriate heat treatment (annealing) is performed once or more before and/or after the plastic processing, as needed. Such heat treatment may be performed in order to enhance the antifouling property or antibiotic properties (bactericidal and sterilizing properties) of the copper alloy material.

In the first to eighth copper alloy materials, Cu and Zn are necessary for controlling leaching of the copper ions from the copper alloy material under seawater, ensuring strength sufficient for cultivation nets or the like, and preventing the material from being worn out by contact with waves and fish and contact with other parts of the material. These effects cannot be sufficiently produced if the Cu content is less than 62 mass %. The corrosion resistance also becomes poor. Also, a Cu content of more than 91 mass % cannot achieve sufficient seawater resistance, and the strength and the wear resistance become poor. In order for Cu and Zn to ensure sufficient strength, corrosion resistance, and seawater resistance, the Cu content should be set at 62 to 91 mass %. For setting the Cu content, the proportions to the other constituent elements must be considered. In particular, the lower limit and upper limit of the Cu content should be set in view of the following considerations, but depending on the ratio of the Sn content to the Zn content. The lower limit should be set so that, first, a more stable corrosion resistance and erosion-corrosion resistance can be ensured and, second, the primary crystal is in an α phase during melt-solidification and involved in peritectic reaction so as to allow grain refining during melt-solidification. The upper limit should be set so that, first, a higher strength and wear resistance are ensured and, second, the copper alloy material has such a low hot deformation resistance as to be extruded through a small diameter, from the viewpoint of cost reduction, if it is prepared by hot extrusion. Third, the upper limit should be set so as to allow peritectic reaction for further grain refining during melt-solidification. In view of these considerations, the Cu content should be set at 62 to 91 mass %, preferably 63 to 82 mass %, and most preferably 64 to 77 mass %. Zn, as well as Cu and Sn, is one of the primary constituents of the (Cu—Zn—Sn-based) alloy composition of the first to eighth copper alloy materials. The Zn helps the occurrence of a peritectic reaction, which refines the crystal grains of the alloy during melt-solidification, reduces the stacking fault energy of the alloy to enhance the flowability of the molten metal and accelerate the reduction of its melting point in a wire forming step, and enhances the corrosion resistance (particularly erosion-corrosion resistance) and mechanical strength (tensile strength, proof stress, impact strength, wear resistance, fatigue strength, etc.) of the resulting wires. In particularly the fifth to eighth copper alloy materials, Zn also accelerates crystal grain refining during melt-solidification and prevents Zr from being lost by oxidation.

In the first to eighth copper alloy materials, Sn is mainly intended to enhance the corrosion resistance (such as seawater resistance). The addition of 0.01 mass % or more of Sn enhances the corrosion resistance, the erosion-corrosion resistance, the wear resistance, and the strength. However, a Sn content of more than 4 mass % does not produce these effects to an extent according to the content. On the contrary, such a Sn content results in a degraded castability (causing cracks, shrinkage cavities, and porous shrinkage cavities), thus degrading the hot workability and cold workability. For use of the copper alloy material for fish cultivation nets, by setting the Sn content at 0.1 mass % or more, the strength of the alloy material of the cultivation nets can be increased. A higher Sn content not only enhances the seawater resistance and erosion-corrosion resistance of the cultivation net material, but also prevents the wires from being worn out by waves or the like effectively to enhance the wear resistance to rubbing by fish or rubbing against each other. This is because Sn-rich corrosion-resistant coatings are formed over the surfaces of the wires and the coatings prevent fish from coming into direct contact with the wires, and the wires from being worn out by the contact with seawater flowing at a high speed. In addition, Sn expands the range of composition in which peritectic reaction (refining crystal grains effectively during melt-solidification) can occur. As the Sn content is increased, the peritectic reaction can occur in compositions having a wider range of Cu content in practice. Accordingly, the Sn content is preferably 0.6 mass % or more, and most preferably 0.8 mass % or more. In contrast, a Sn content of more than 4 mass % allows the γ or δ phase, which is a hard phase having a higher Sn content than the parent phase (a phase), to be notably produced at an area ratio of 10% or more, but depending on the Cu and Zn contents. Consequently, the material can become easy to break during wiredrawing, and the γ phase can be selectively corroded to reduce the seawater resistance. If the net repeatedly suffers strong stresses, the net may result in fatigue fracture. Thus, an excessively high Sn content causes Sn to segregate significantly to degrade the hot ductility and the cold workability and ductility, but depending on the Cu and Zn contents. Furthermore, the range of solidification temperature expands according to the increase of the Sn content, and consequently the castability is degraded. In view of these considerations, the Sn content should be set at 0.01 to 4 mass %, preferably 0.1 to 3 mass %, more preferably 0.6 to 3 mass %, and most preferably 0.8 to 2.5 mass % so as to establish an appropriate ratio of the γ phase to the δ phase. In order to form the γ phase and the δ phase at a ratio in the above range and melt and disperse the Sn uniformly as much as possible, it is preferable that the alloy composition be adjusted so that the compositional value $Y9=0.06[Cu]-[Sn]$ derived from the Cu and Sn contents is 1 to 4.5 (preferably 1.5 to 4.2, more preferably 2 to 3.8, most preferably 2.5 to 3.5).

In the fifth to eighth copper alloy materials, Zr and P are added in order to refine the crystal grains of the resulting copper alloy, particularly the crystal grains after melt-solidification. Although singly used Zr or P can only slightly reduce the crystal grain size of the alloy, as well as other common additive elements, a combined use of Zr and P can refine the crystal grains remarkably effectively. This effect of refining the crystal grains is exerted when the Zr content is 0.0008 mass % or more, preferably 0.002 mass % or more, more preferably 0.004 mass % or more, and most preferably 0.006 mass % or more, and when the P content is 0.01 mass % or more, preferably 0.02 mass % or more, more preferably 0.025 mass % or more, and most preferably 0.035 mass % or more. However, if the Zr content reaches 0.045 mass % or the P content reaches 0.25 mass %, the effect of combined use of Zr and P in crystal grain refining is completely saturated regardless of other constituents and their contents. Hence, the Zr and the P content capable of exerting this effect effectively are 0.045 mass % or less and 0.25 mass % or less, respectively. Such low Zr and P contents set in the above ranges do not inhibit the characteristics derived from the other constituents of the resulting alloy. On the contrary, such Zr and P contents allow crystal grain refining, so that Sn can be uniformly dispersed without forming a series of regions having a high content of segregated Sn. Consequently, cast cracks can be prevented and healthy cast with a low microporosity can be produced. Furthermore, the workability in cold drawing and cold extraction can be enhanced, and thus, the characteristics of the resulting alloy can be enhanced. In other words, by adding small amounts of Zr and P, the Cu—Zn—Sn-based copper alloys can be modified so as to have a smaller crystal grain size than their corresponding alloys containing the same constituents except Zr and P (like, for example, the alloy of the fifth copper alloy material corresponding to the first copper alloy material, the alloy of the sixth copper alloy material corresponding to the second copper alloy material, the alloy of the seventh copper alloy material corresponding to the third copper alloy material, and the alloy of the eighth copper alloy material corresponding to the fourth copper alloy material) while ensuring characteristics superior or equivalent to their original characteristics.

Zr has an extremely high affinity for oxygen. Accordingly, if raw materials are melted in air or if scraps (waste cultivation nets) are used as the raw materials, Zr is liable to form oxides or sulfides. Addition of an excessive amount of Zr increases the viscosity of molten metal. The molten metal traps oxides or sulfides during casting, and cast defects thus occur which easily result in blowholes or microporosities. In order to prevent this, melting and casting can be performed in a vacuum or a complete inert gas atmosphere. This however limits the versatility of the process and increases the costs of copper alloys containing Zr as a grain-refining element. In view of these considerations, the Zr content is preferably set so as not to form oxides or sulfides. Such a Zr content is preferably 0.0290 mass % or less, more preferably 0.0240 mass % or less, and most preferably 0.0190 mass % or less. A Zr content in these ranges reduces the formation of zirconium oxides or sulfides and thus makes it possible to produce a healthy copper alloy material constituted of fine crystal grains, even if the fifth to eighth copper alloy materials are reused and melted in air.

Accordingly, the Zr content should be 0.0008 to 0.045 mass %, preferably 0.002 to 0.029 mass %, more preferably 0.004 to 0.024 mass %, and most preferably 0.006 to 0.019 mass %.

In the fifth to eighth copper alloy materials, P is added in combination with Zr, as described above, to refine the crystal grains. P, however, affects the seawater resistance, corrosion resistance, castability, and cold and hot ductility. In view of the effects of P on the seawater resistance, the corrosion resistance, the castability, and the cold and hot ductility in addition to the effect of combined use of P and Zr in refining the crystal grains, the P content should be set at 0.01 to 0.25 mass %, preferably 0.02 to 0.18 mass %, more preferably 0.025 to 0.15 mass %, and most preferably 0.035 to 0.12 mass %.

The present invention is also directed to a method for manufacturing copper alloy materials, particularly the fifth to eighth copper alloy materials. In the method, Zr in copper alloy form is added immediately before pouring in a casting step so that addition of oxides or sulfides of Zr can be prevented in this step. In the casting step of the casting material used in the manufacture of the fifth to eighth copper alloy materials, it is preferable that Zr be added in a form of granular or thin-plate intermediate alloy (copper alloy) immediately before pouring so that addition of Zr in form of oxide or sulfide is prevented. Since Zr is easy to oxidize, as described above, it may be advantageous that, in casting, to add Zr immediately before pouring. In this instance, the Zr is preferably in an intermediate alloy form of granules (grain size: about 2 to 50 mm) or thin plate (thickness: about 1 to 10 mm) having a low melting point close to the melting point of the targeted copper alloy and containing many types of constituents (for example, in a form of Cu—Zr or Cu—Zn—Zr alloy containing mainly 0.5 to 65 mass % of Zr, and 0.1 to 5 mass % each of at least one element selected from the group consisting of P, Mg, Al, Sn, Mn, and B), because the melting point of Zr is 800 to 1000° C. higher than that of the targeted copper alloy. In particular, in order to reduce the melting point so that the Zr can be easily melted, and in order to prevent Zr from being lost by oxidation, a Cu—Zn—Zr-based alloy containing 0.2 to 35 mass % of Zr and 15 to 50 mass % of Zn (more preferably 1 to 15 mass % of Zr and 25 to 45 mass % of Zn) is preferably used. Zr impairs the electrical and thermal conductivities, which are inherent characteristics of copper alloys, but depending on the proportion to P used in combination with Zr. However, if the content of Zr in a form of non-oxide or non-sulfide is 0.045 mass % or less (particularly 0.019 mass % or less), the electrical and thermal conductivities are hardly reduced by addition of Zr. Even if the electrical or thermal conductivity is reduced, the degree of the reduction is very small in comparison with when Zr is not added.

In the fifth to eighth copper alloy material, single use of Sn singly does not much enhance the grain-refining effect. However, Sn used in combination with Zr and P notably exerts the grain-refining effect. Sn enhances the mechanical properties (for example, strength), the corrosion resistance, and the wear resistance. Besides, Sn breaks dendrite arms, or expands the possible ranges of contents of Cu and Zn, which are involved in peritectic reaction, to help peritectic reaction effectively. Sn thus helps the granulation or refining of the crystal grains effectively, and this function of Sn is notably exerted particularly in the presence of Zr (and P). The γ phase produced by adding Sn hinders the growth of crystal grains after melt-solidification, thus contributing to the grain refining of the crystal grains. γ Phases are formed from regions having a high Sn content. Since the regions having a high Sn content are uniformly and finely dispersed in the stage of melt-solidification, the resulting γ phases are also finely dispersed, and consequently hinder the growth of α crystal grains at high temperatures after solidification. The fine dispersion of the γ phase leads to a high corrosion resistance and wear resistance. It is therefore preferable that, in order to produce the effect of the combined use of Zr and P in refining the crystal grains of the fifth to eighth copper alloy materials, the Zr and the P content be set with consideration of their relationship and the relationship with the Sn content. Specifically, their proportions Z1 (=[P]/[Zr]), Z2 (=[Sn]/[Zr]), and Z3 (=[Sn]/[P]) are preferably set in the above ranges. Among these proportions, Z1 or the proportion of P to Zr is important in refining the crystal grains. If the proportion Z1 is in the above range (Z1=0.5 to 150), the rate of crystal nucleation is higher than that of crystal growth during melt-solidification. Consequently, even the grains of a melt-solidified product can be refined to an extent equivalent to the grains of hot-worked material or recrystallized material. In particular, by setting the proportion Z1 of P to Zr at 0.8 to 50, the degree of crystal grain refining can be improved. A Z1 value of 1.5 to 15 further improves the degree of crystal grain refining; and a Z1 value of 2.0 to 12 still further improves the degree.

The element X1 (at least one element selected from the group consisting of As, Sb, Mg, and P) contained in the second and fourth copper alloy materials and the element X3 (at least one element selected from the group consisting of As, Sb, and Mg) contained in the sixth and eighth copper alloy materials are mainly intended to enhance the corrosion resistance (particularly dezincification corrosion resistance). The addition of 0.02 mass % or more of Sb or As enhances the seawater resistance and the corrosion resistance. In order for these elements to produce the effect of enhancing the corrosion resistance notably, Sb or As is added preferably in an amount of 0.03 mass % or more. However, a Sb or As content of more than 0.25 mass % does not produce this effect to an extent according to the content and reduces the ductility (ease of wiredrawing) of the material. In view of the decrease of ductility, the Sb content and the As content each should be set at 0.25 mass % or less. In addition, in view of the hot workability and the cold workability, their contents are each preferably set at 0.12 mass % or less. Hence, the As and the Sb content each should be 0.02 to 0.25 mass %, and preferably 0.03 to 0.12 mass %.

The raw materials of the copper alloy often include scraps (waste heat exchanger tubes), and the scraps often contain S (sulfur). In use of S-containing scraps as raw materials of an alloy, Mg being element X1 or X3 enhances the flowability of molten metal in casting, as well as enhancing the corrosion resistance. Mg can remove constituent S by forming MgS, which has a less negative effect than S. Since the MgS does not adversely affect the corrosion resistance even if it remains in the resulting alloy, Mg can prevent the degradation of the corrosion resistance resulting from the presence of S in the raw material, effectively. Constituent S in the raw material is liable to be present in grain boundaries and consequently may corrode the grain boundaries. The addition of Mg can prevent the grain boundary corrosion effectively. In order to produce such an effect, the Mg content should be set at 0.001 to 0.2 mass %, preferably 0.002 to 0.15 mass %, and more preferably 0.005 to 0.1 mass %. In the sixth and eighth copper alloy materials, the molten metal may have such a high S content as S consumes Zr, disadvantageously. By adding 0.001 mass % or more of Mg to the molten metal before adding Zr, the constituent S in the molten metal is removed by forming MgS. Thus, the above problem does not occur. However, if the Mg content is more than 0.2 mass %, Mg is oxidized, as in the case of Zr, to increase the viscosity in melting. Consequently, for example, trapped oxides may bring about a cast defect. In the case where Mg is used as X3, therefore, the Mg content is set in the above range.

P used as X1 contributes to the increase of seawater resistivity and increases the flowability of the molten metal. These effects are exerted at a P content of 0.01 mass % or more, preferably 0.018 mass % or more, more preferably 0.15 mass % or more, and most preferably 0.12 mass % or more. However, an excessive P may adversely affect the cold and hot ductilities and the castability. In view of this, the P content should be set at 0.25 mass % or less, preferably 0.18 mass % or less, more preferably 0.15 mass % or less, and most preferably 0.12 mass % or less. Hence, the content of P used as X1 should be 0.01 to 0.25 mass %, preferably 0.02 to 0.018 mass %, more preferably 0.025 to 0.15 mass %, and most preferably 0.035 to 0.12 mass %, as in the case of the P used as a necessary constituent in the fifth to eighth copper alloy materials.

In the third and fourth copper alloy materials or the seventh and eighth copper alloy materials, element X2 or X4, which is at least one element selected from the group consisting of Al, Si, Mn, and Ni, is added in order to mainly enhance the strength, the flowability, the erosion-corrosion resistance at a high flow rate, and the wear resistance. In particular, the addition of the element X2 or X4 is advantageous when the copper alloy material is used as wires or bars forming seawater netted structures (for example, fish cultivation nets). By adding the element X2 or X4, the wear and tear of the wires or bars can be prevented effectively even under harsh conditions (when the cultivation net is placed in an offing whose environmental conditions are strongly influenced by waves, or when the net is used for cultivation of large, fast migratory fish that hits the net to give it a large impact, such as yellowtail or tuna). For example, a seawater netted structure formed of a large number of wires (particularly fish cultivation net) can be worn out or torn rapidly by seawater or waves running at a high speed, by contact with or hit by cultured fish, or by rubbing of the wires against each other. Al and Si each form a strong, corrosion-resistant Al—Sn or Si—Sn coating over the surface of the wires. The coating enhances the wear resistance of the wires to prevent the wear and tear of the wires as much as possible. A combination of Mn and Sn also forms a corrosion-resistant coating. Specifically, Mn can form an intermetallic compound by combined use with Si and further enhance the wear resistance of the wires; hence, Mn mainly has the effect of forming an intermetallic compound preventing the wear and tear of the wires. X2 enhances the flowability of molten metal in casting, as well as enhancing the wear resistance. In order for X2 to produce these effects, 0.02 mass % or more of Al or Si should be added (for Al, 0.05 mass % or more is preferable and 0.1 mass % or more is much preferable; for Si, 0.1 mass % or more is preferable). If Mn is added, the Mn content should be 0.05 mass % or more (preferably 0.2 mass % or more). However, if more than 1.5 mass % of Mn or Al is added, the ductility is degraded to adversely affect wiredrawing. In particular, when the resulting cultivation net is used under the above-described harsh conditions, the materials of the net can be cracked or broken by repeated bending or the like. In order to prevent the degradation of ductility and the crack or breakage resulting from repeated bending, effectively, the Si content should be 1.9 mass % or less and the Al and Mn contents each should be 1.5 mass % or less (for Al, 1.2 mass % or less is preferable and 1 mass % or less is more preferable; for Si and Mn, 1 mass % or less is preferable). If Al is used as X2 or X4, it can form a dense oxide coating over the surface of the copper alloy by appropriate heat treatment (annealing), thus further enhancing the durability. In this instance, the Al content is preferably set at 0.1 to 1 mass %, and the heat treatment is preferably performed at a low temperature for a long time. Specifically, the heat treatment is preferably performed at a temperature of 400 to 470° C. for 30 minutes to 8 hours. The Ni content should be set at 0.005 mass % or more from the viewpoint of enhancing the corrosion resistance. In view of the influence of Ni on the hot workability and the consumption (inhibiting crystal grain refining) by Ni of Zr and P, which are useful in refining crystal grains in the seventh and eighth copper alloy materials, the Ni content is preferably 0.5 mass % or less (more preferably 0.1 mass % or less).

In the first to eighth copper alloy materials, in order to ensure the resulting netted structure (for example, a fish cultivation net) has characteristics (seawater resistance, wear resistance, ductility, strength, etc.) sufficient to be used under or in contact with seawater, the alloy material should have the above-described composition and include α, γ, and δ phases at a total area ratio of 95 to 100% (preferably 98 to 100%, more preferably 99.5 to 100%). An excessive γ and/or δ phase easily causes the alloy material to break during wiredrawing, and particularly brings the γ phase into selective corrosion to degrade the seawater resistance. Although the γ phase enhances the wear resistance and the erosion-corrosion resistance and the δ phase enhances the erosion-corrosion resistance, the presence of the γ and/or δ phase degrades the ductility. In order to bring the strength, wear resistance, and ductility into balance without breaking by wiredrawing or degrading the seawater resistance, the alloy material has the above-described composition and, preferably, the total area ratio of the γ and δ phases is set at 0 to 10% (preferably 0 to 5%, more preferably 0 to 3%). The phase structure may be occupied by 95 to 100% of α phase (preferably 98 to 100%, more preferably 99.5 to 100%), containing neither γ nor δ phase (for example, the phase structure is essentially composed of only the α phase, or the α and β phases), depending on the process of plastic processing for manufacturing the first to eighth copper alloy materials. If the γ phase is present, it is preferable that the γ phase be fractured (preferably, into elliptical fragments with a length of 0.2 mm or less) from the viewpoint of minimizing the selective corrosion by the γ phase and the degradation of ductility. Since a series of β phase fragments reduces the seawater resistance, the β phase should not be formed in view of the seawater resistance. However, the formation of the β phase enhances the hot workability (particularly extrusion workability). Accordingly, the content (area ratio) of the β phase is preferably 5% or less (preferably 2% or less, more preferably 0.5% or less). If the seawater resistance is particularly important, it is preferable that the phase structure do not include the β phase. If any of the first to eighth copper alloy materials has a phase structure including the γ phase and/or the β phase, the copper alloy material is preferably subjected to appropriate heat treatment (for example, annealing at a temperature of 450 to 600° C. for 0.5 to 8 hours) to fracture the γ and β phases into spherical fragments. By fracturing the γ and β phases into spherical fragments, the negative effect resulting from the formation of the γ and β phases can be eliminated as much as possible. In the presence of fractured spherical γ phase fragments, for example, the degradation of ductility, which results from the formation of the γ phase, is reduced and the wear resistance is enhanced. The heat treatment is performed by, for example, homogenization annealing (heat treatment at a temperature of 450 to 600° C. and cooling to 450° C.) of the copper alloy material or its intermediate product, and preferably by subsequent finish annealing at a temperature of 400 to 470° C. Since the combined use of Zr and P refines crystal grains to fracture the γ phase into spherical fragments inevitably, the γ phase can be more uniformly dispersed.

In order to provide the above-described phase structure in the first to eighth copper alloy materials, the Sn content should be controlled according to the proportions to the Cu and the Zn content. Specifically, the contents of the constituent elements should be set so that the compositional values Y1 to Y8 are each in the range of 62 to 90 (preferably 62.5 to 81, more preferably 63 to 76, most preferably 64 to 74). The lower limits of Y1 to Y8 are set as described above so that the proportions of the main constituents Cu, Sn, and Zn ensure a superior seawater resistance, erosion-corrosion resistance, and wear resistance. In addition, in view of the cold-drawability, ductility, corrosion resistance and castability associated with the γ and/or δ phase, the upper limits of Y1 to Y8 should be set as described above. In order to ensure these properties, the Sn content is varied depending on the Cu content. In the fifth to eighth copper alloy materials, Zr and P are added mainly for crystal grain refining. If the first to fourth copper alloy materials, which do not contain such grain-refining elements, are produced in wire or thin bar by hot extrusion, it is preferable that the deformation resistance in the extrusion be reduced in view of cost. In order to reduce the deformation resistance as much as possible, it is preferable that the Cu content be set at 63.5 to 68 mass % (more preferably 64 to 67 mass %) and that the compositions of the alloys be set so that Y1 to Y8 satisfy the above ranges.

The fifth to eighth copper alloy materials achieve refined crystal grains by adding Zr and P, and have an average grain size of 0.2 mm or less (preferably 0.1 mm or less, most preferably 0.06 mm or less) after melt-solidification. The materials can be produced in wire or bar form by continuous casting, such as upward casting (up-casting), and the resulting wire or bar can be put into practical use. Also, the number of steps in the plastic processing for preparing plastic-processed or combination-processed wires or bars can be reduced, and thus the manufacturing costs can be greatly reduced. If the crystal grains are not refined, repeated heat treatments (including homogenization annealing) are required to remove the dendrite structure peculiar to cast metal and segregated Sn and to fracture the γ phase into spherical fragments. Also, coarse crystal grains degrade the surface state of the resulting material. This easily causes cracks during plastic processing (wiredrawing or drawing) for forming wires or bars, in association with the segregation of Sn. Thus, the number of the steps of plastic processing for preparing targeted plastic-processed wires or bars is significantly increased. In contrast, if the crystal grains are refined as described above, homogenization annealing is not necessary because segregation is microscopic. Consequently, the number of the steps of plastic processing and heat treatment for forming plastic-processed products (particularly wires or thin bars) being the fifth to eighth copper alloy materials can be greatly reduced. For example, by applying wiredrawing or drawing once (wiredrawing twice including finish wiredrawing for adjusting the temper) and heat treatment (annealing) once to a casting material or a cast-processed material, the resulting fifth to eighth copper alloy materials can have high quality and can be used suitably for cultivation nets or the like. For example, in the formation of wires by wiredrawing, since crystal grain refining enhances the ductility and reduces asperities at the surface of the copper alloy material, breakage during wiredrawing can be prevented. For facing (such as healing) of the surface of the copper alloy material, the cutting allowance can be small. In the case where the γ and/or δ phase precipitates, the phase is present in the grain boundary, and the smaller the crystal grains are, the shorter the phase length is. Accordingly, a special step for fracturing the γ and/or δ phase is not required, or if required, the step can be kept at minimum. Thus the number of steps in the manufacturing process can be greatly reduced, and accordingly the manufacturing costs can be reduced as much as possible. It goes without saying that wires or bars from which segregation is not eliminated do not have satisfactory characteristics, including corrosion resistance and mechanical properties.

Since the fifth to eighth copper alloy materials achieve refined crystal grains, as described above, the Sn and the Cu content can be increased without segregation of Sn resulting from a high Sn content, or degradation of extrusion workability due to the increase of hot deformation resistance resulting from a high Cu content. Specifically, while a high Sn content of 1 to 1.5 mass % or more promises to increase the corrosion resistance or other properties greatly, the high content of Sn brings about segregation so significantly as to easily form cracks, shrinkage cavities, blowholes, or microporosities during melt-solidification, and besides cracks during hot working. However, if crystal grains are refined during melt-solidification, these problems do not occur and the Sn content therefore can be increased to further enhance the seawater resistance. A high Cu content (Cu content: 68 mass % or more) increases the hot deformation resistance to degrade the hot workability notably, particularly extrusion workability. However, if the crystal grains are refined, this problem does not occur and the degradation of hot workability can be prevented even if the Cu content is high.

In the fifth to eighth copper alloy materials, the addition of Zr and P is performed to refine the crystal grains, but does not impair the inherent characteristics of the copper alloy. The crystal grain refining by addition of Zr and P ensures characteristics superior or equivalent to the original characteristics of the corresponding copper alloy material containing the same constituents except the grain-refining elements Zr and P, as described above. In order to reduce the average grain size after melt-solidification to the above-described level, the ratio Z1 of P to Zr, which are grain-refining elements, and the ratios of Sn to Zr and Sn to P, namely Z2 and Z3, are set in the above ranges, in addition to setting the Sn content and other contents so that the copper alloy material has a composition and phase structure satisfying the compositional values Y1, Y3, and Y4, as described above.

According to a second aspect of the present invention, a netted structure used in seawater is provided which is formed of any one of the first to eighth copper alloy materials and which leads to, for example, practical copper nets having superior characteristics for fish cultivation (antifouling property, bactericidal and sterilizing properties, etc.).

The seawater netted structure of the present invention is formed of copper alloy wires or bars being any one of the first to eighth materials. The netted structure is formed of plastic-processed, cast-processed, or combination-processed wires or bars in a wire netting or grid.

Preferably, the seawater netted structure of the present invention is made by forming wires being any one of the first to fourth copper alloy materials or the fifth to eighth copper alloy materials into wire netting. Preferably, the netted structure has a rhombically netted form made by arranging a large number of waved wires in parallel such that the adjacent wires are entwined with each other at their curved portions. The seawater netted structure is mainly used as a fish cultivation net. The cultivation net has a ring-shaped reinforcing frame along the lower edge of the net. The reinforcing frame maintains the shape of the lower edge of the net, and it is preferably spread with downward tension. By maintaining the shape by the reinforcing frame and by applying such tension, the wires can be prevented as much as possible from rubbing against each other at the entwined portions. The reinforcing frame is preferably formed by a pipe made of a copper alloy having the same composition as the material of the net (wires being any one of the first to eighth copper alloy materials).

In addition to the cultivation net made of any one of the first to fourth or the fifth to eighth copper alloy materials (wires), the seawater netted structure of the present invention may be a seawater intake or the like formed of any one of the bar-shaped first to fourth or fifth to eighth copper alloy materials (bars) in a grid manner by welding or the like.

If the wire (netting wire) used for the fish cultivation net or the like is any one of the first to fourth copper alloy materials (plastic-processed materials), the wire is prepared by, for example, repeatedly drawing and annealing a wire (diameter: 10 to 25 mm) formed by extrusion of a casting material (billet, ingot, or the like) into a diameter of 3 to 4 mm. In this instance, this wiredrawing is repeated several times depending on the difference in diameter between the extruded wire and the netting wire (percentage of wiredrawing). If the netting wire is any one of the fifth to eighth copper alloy materials, the netting wire is formed by, for example, drawing a cast wire (diameter: 5 to 10 mm) formed by horizontal continuous casting or upward casting (up-casting) into a diameter of 3 to 4 mm and subsequently annealing once or twice. The cast-processed wire formed by horizontal continuous casting or upward casting (up-casting) still contains segregated Sn, and accordingly it may not be suitable for cultivation nets. However, it can be suitably used for seawater netted structures other than the cultivation nets.

Advantages

The first to eighth copper alloy materials have extremely superior seawater resistance and durability to the known copper alloy materials. In use for a seawater netted structure used under or in contact with seawater, such as a fish cultivation net, the copper alloy materials can prevent the corrosion and the wear and tear of the netted structure by seawater, waves, and cultured fish as much as possible, thereby increasing the lifetime of the structure. Accordingly, these copper alloy materials can extend the application of the seawater netted structure to the fields where it has not been used for the reason of the total cost including the lifetime of the alloy, using the superior characteristics (antibiotic property, antifouling property, etc.) of the copper alloy to those of other metals effectively.

In particular in the fifth to eighth copper alloy materials, the crystal grains are refined after melt-solidification, that is, grain refining in the cast structure is achieved in terms of not only macroscopic structure but also microscopic structure, by adding small amounts of Zr and P. The above characteristics of these copper alloy materials can be improved more than those of not only the known copper alloy material but also the first to fourth copper alloy materials (copper alloy materials before improvement) containing the same constituent elements except Zr or P. Furthermore, since the crystal grains are refined during casting, the castability can be greatly enhanced and the plastic workability of the copper alloy can be improved. Thus, the fifth to eighth copper alloy materials allow satisfactory plastic processing, such as extrusion or wiredrawing, after casting.

In the seawater netted structure, particularly a fish cultivation net, made of any one of the first to eighth copper alloy materials, the durability, which is a fault in the known copper nets, can be greatly enhanced to the extent that the net can be used in practice in view of the total cost without adversely affecting advantages of the known copper nets. By using the fish cultivation net made of any one of the first to eighth copper alloy materials, any type of fish including large migratory fish can be cultured healthily and economically. In particular, for the fish cultivation net or the like made of any one of the fifth to eighth copper alloy materials, the material can be prepared only by about one or two wiredrawing operations (or by a casting process not requiring even wiredrawing, depending on the conditions or application where the seawater netted structure is used) without extrusion. Accordingly, the number of steps for such processing can be reduced without a large casting or extrusion system, and thus manufacturing costs can be greatly reduced.

Figure 1:
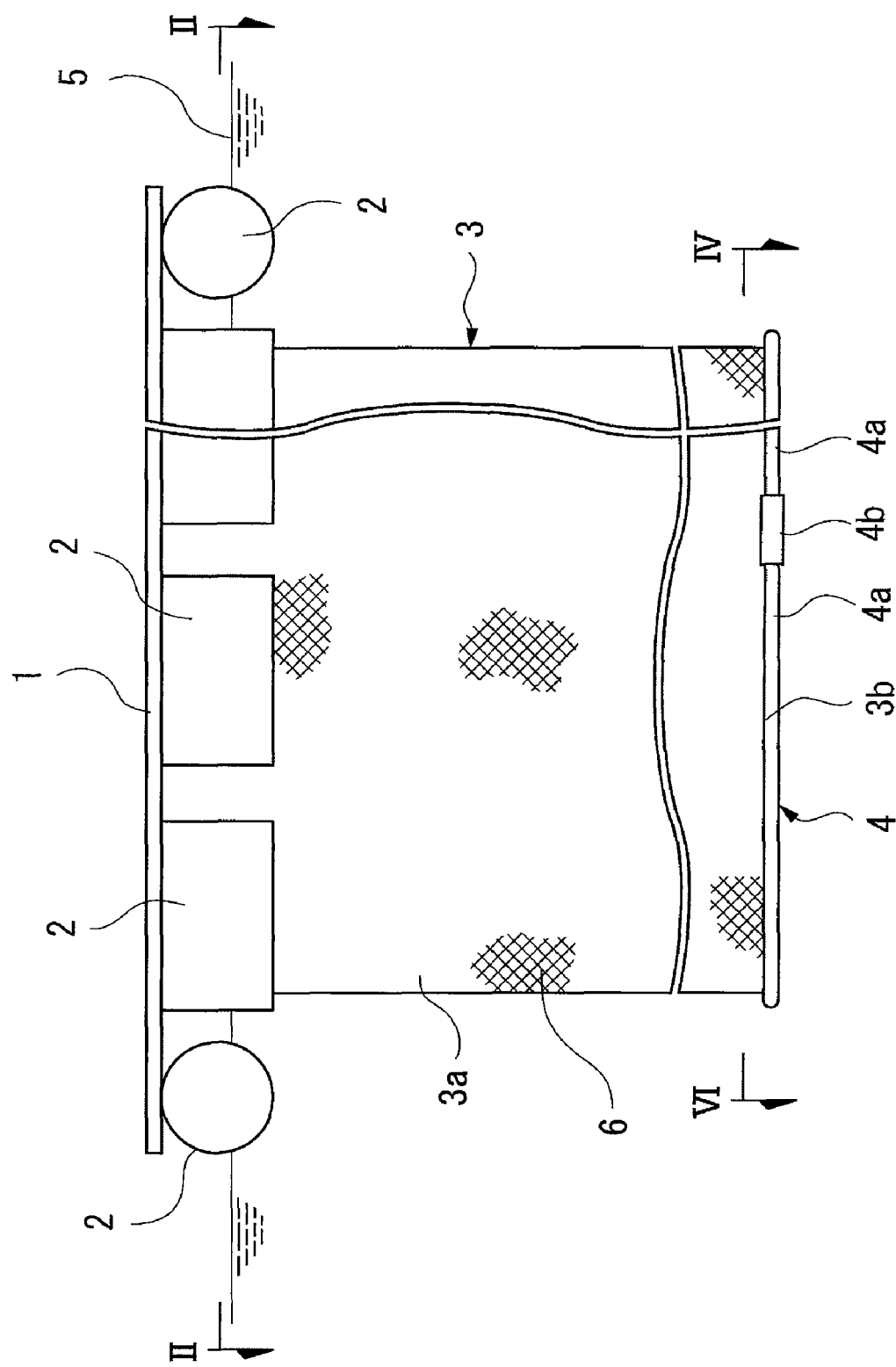
FIG. 1 is a front view of a fish preserve using a fish cultivation net being a seawater netted structure according to the present invention.

| Reference Numerals | |
| --- | --- |
| 1: | support frame |
| 2: | float |
| 3: | fish cultivation net (seawater netted structure) |
| 3a: | periphery |
| 3b: | bottom |
| 4: | reinforcing frame |
| 4a: | straight pipe |
| 4b: | L-shaped pipe |
| 5: | surface of the sea |

| -continued | |
| --- | --- |
| Reference Numerals | |
| 6: | netting wire (wire) |
| 6a: | curved portion (entwined portion) |

BEST MODE FOR CARRYING OUT THE INVENTION

Figure 2:
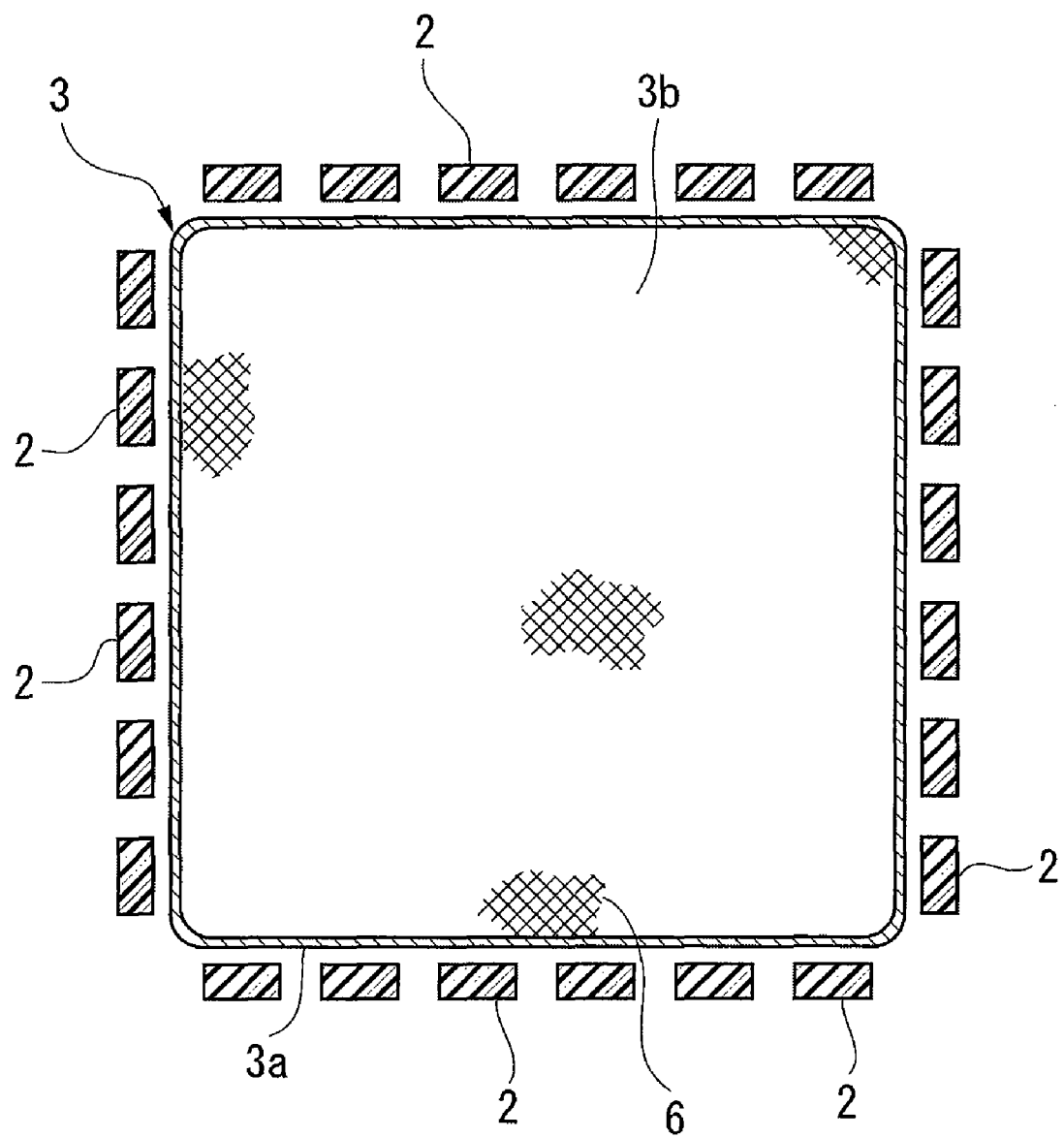
FIG. 2 is a transverse sectional view taken along line II-II of FIG. 1.
Figure 3:
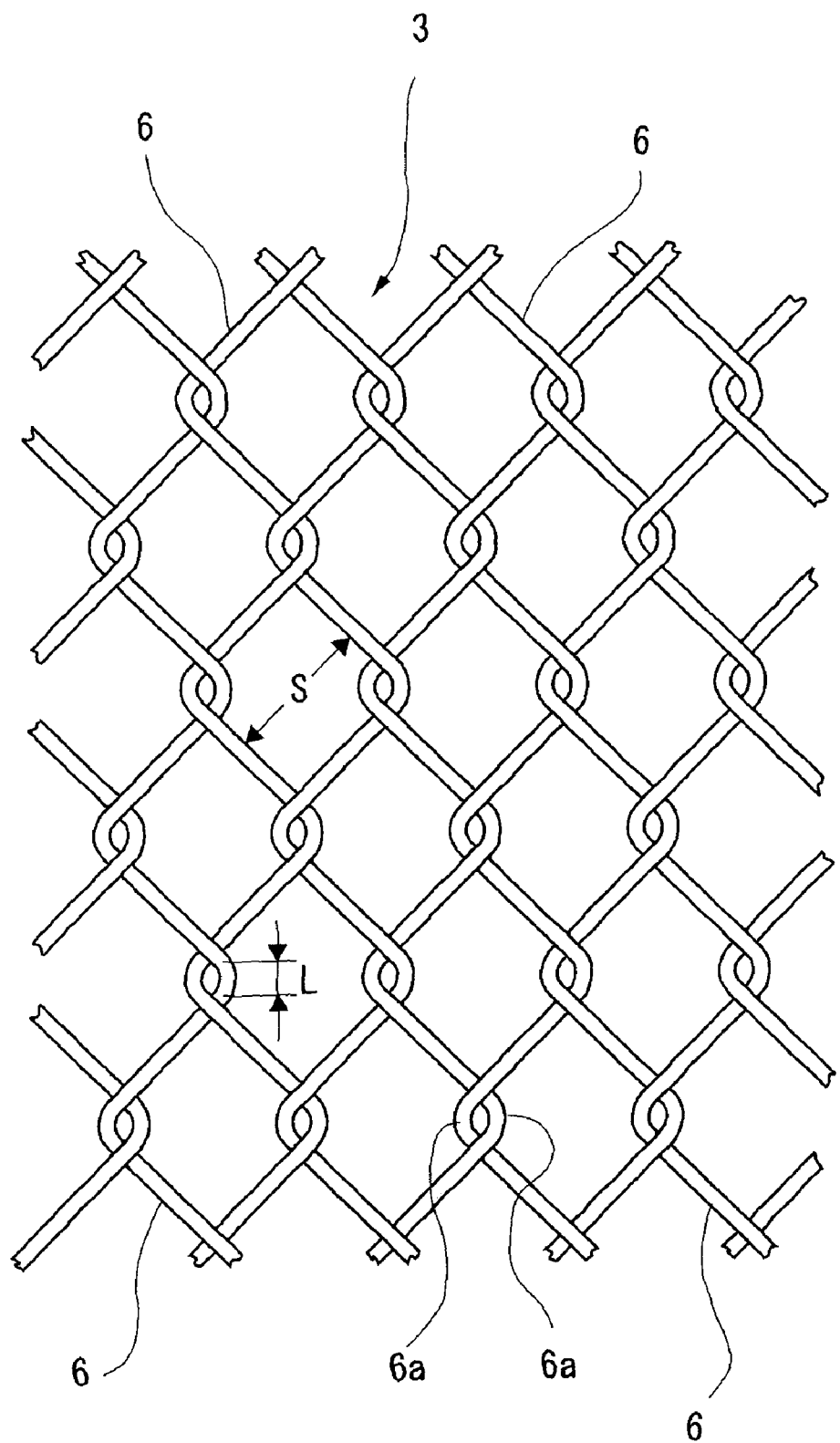
FIG. 3 is a fragmentary enlarged front view of the cultivation net.
Figure 4:
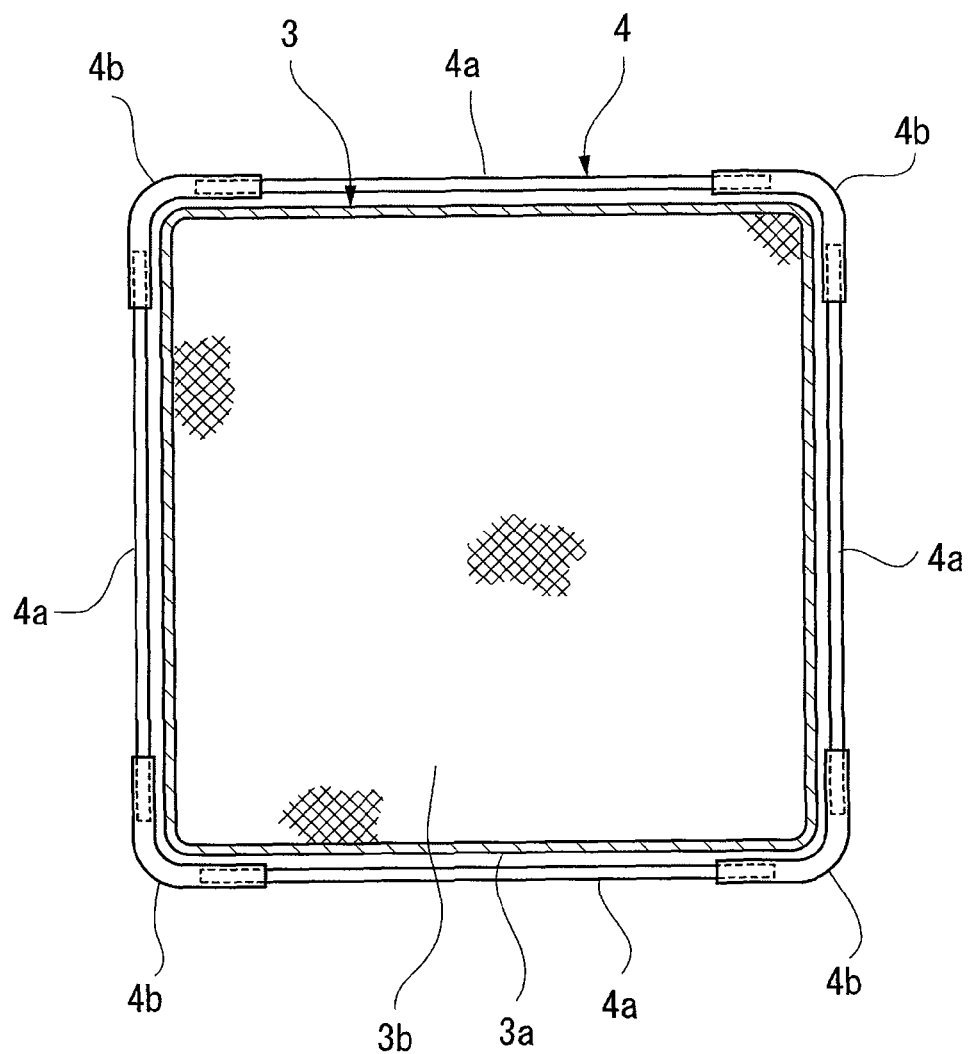
FIG. 4 is a transverse sectional view taken along line IV-IV of FIG. 1.

FIG. 1 is a front view of a fish preserve using a fish cultivation net being a seawater netted structure according to the present invention, and FIG. 2 is a transverse sectional view taken along line II-II of FIG. 1. FIG. 3 is a fragmentary enlarged front view of the cultivation net, and FIG. 4 is a transverse sectional view taken along line IV-IV of FIG. 1.

As shown in FIG. 1, the fish preserve includes a support frame 1, a plurality of floats 2 attached to the support frame 1, and a fish cultivation net 3 hanging from the support frame 1. A reinforcing frame 4 is also attached to the lower edge of the cultivation net 3.

The support frame 1 is formed of a metal (for example, iron) square bar, plate, pipe, or the like in a square or rectangular frame form. The support frame 1 doubles as a foothold for cultivation work. The inner periphery of the support frame 1 has an attachment with which the upper edge of the cultivation net 3 is held. The floats 2 are made of expanded polystyrene and attached to the bottom surface of the support frame 1 along the upper edge periphery of the cultivation net 3 in a rectangular ring manner. The floats 2 hold the fish preserve in such a manner as to float the support frame 1 on the surface 5 of the sea.

The cultivation net 3, which is formed of copper alloy netting wires 6 with a known net forming machine (metal netting machine) used for manufacturing iron nets, includes a square or rectangular tube-like periphery 3a whose upper edge is joined to the attachment provided at the inner periphery of the support frame 1 with wire ropes or the like, and a square or rectangular bottom 3b closing the lower edge, as shown in FIGS. 1 and 2. Specifically, the cultivation net 3 has a rhombically netted structure made by arranging a large number of waved netting wires 6 in parallel such that the curved portions 6a of each netting wire 6 are entwined with the curved portions 6a of the adjacent netting wires 6, as shown in FIG. 3. Any one of the first to fourth copper alloy materials (for example, plastic-processed material A in Example 1) or fifth to eighth copper alloy materials (for example, combination-processed material B (or cast-processed material) in Example 2) is used as the netting wire 6. The shape (lengths of the sides of the periphery 3a, dimensions of the mesh S (see FIG. 3), etc.) of the cultivation net 3 is selected according to the installation site, the type of cultured fish, and the culturing conditions.

The reinforcing frame 4 has a square or rectangular ring structure formed by connecting four straight pipes 4a with four L-shaped pipes 4b, as shown in FIG. 4, and is attached to the lower edge of the cultivation net 3 in such a manner as to surround the bottom 3b. The pipes 4a and 4b are made of the same copper alloy as the netting wire 6. The connection of the straight pipes 4a to the L-shaped pipes 4b is such that they permit relative displacement to some extent in the direction of their axes so as to be able to follow the deformation of the cultivation net 3 caused by, for example, waves.

The reinforcing frame 4 reinforces the lower edge of the cultivation net 3 to maintain its shape. The shape of the cultivation net 3 is thus maintained at both the upper and lower edges by the support frame 1 and the reinforcing frame 4; hence, the whole shape can be maintained appropriately without being largely deformed by waves, large migratory fish, or the like. The reinforcing frame 4 places downward tension on the periphery 3a of the cultivation net 3 due to its own weight. The reinforcing frame 4 thus functions as a tension-applying member (anchor) for reducing the clearances L (see FIG. 3) between the entwined portions 6a of the netting wires 6 of the periphery 3a of the cultivation net 3 to a uniform small size. The weight of the reinforcing frame 4 is preferably set so as to apply such a tension as the clearance L becomes 0.1 to 10 mm (preferably 0.5 to 5 mm).

The rubbing of the netting wires 6 against each other at the entwined portions 6a can be prevented effectively by remaining the shape of the fish cultivation net 3 with the support frame 1 and the reinforcing frame 4 and reducing the clearance L with the tension of the reinforcing frame 4. Thus, the wear and tear resulting from the relative movement of adjacent netting wires 6 can be prevented as much as possible. The reinforcing frame 4 is used as the occasion arises, but may not be used depending on the type of cultured fish or the environment where the cultivation net 3 is used.

EXAMPLES

Example 1 prepared plastic-processed materials in wire form (hereinafter collectively referred to as plastic-processed wires A) having compositions shown in Table 1: Nos. 101 to 108, Nos. 201 to 206, Nos. 301 to 305, and Nos. 401 to 405. Wires No. 101 to 108 belong to the first copper alloy material; wires Nos. 201 to 206 belong to the second copper alloy material; wires Nos. 301 to 305 belong to the third copper alloy material; wires Nos. 401 to 405 belong to the fourth copper alloy material.

The plastic-processed wires Nos. 101 to 108, Nos. 201 to 206, Nos. 301 to 305, and Nos. 401 to 405 were each prepared as follows. First, a cylindrical ingot A-1 having the corresponding composition shown in Table 1 was hot extruded into a round bar A-2 of 12 mm in diameter. Specifically, the compositions containing 68 mass % or more of Cu, which have high hot deformation resistances, were formed into cylindrical ingots A-1 with a diameter of 60 mm and a length of 100 mm, and were then hot extruded into round bars A-2 at 850° C. The compositions containing less than 68 mass % of Cu were formed into cylindrical ingots A-1 with a diameter of 100 mm and a length of 150 mm, and were then hot extruded into round bars A-2 at 800° C. Then, the round bars A-2 were each subjected to cold wiredrawing to form a primary processed wire A-3 of 9 mm in diameter. This wiredrawing was performed through the two steps of: drawing a round bar A-2 into an intermediate wire of 10.2 mm in diameter; and further drawing the intermediate wire into a primary processed wire A-3 of 9 mm in diameter. The primary processed wire A-3 was allowed to stand at 550° C. for an hour and then subjected to cold wiredrawing to form a secondary processed wire A-4 of 6 mm in diameter. The secondary processed wire A-4 was further subjected to cold wiredrawing to form a tertiary processed wire A-5 of 4.3 mm in diameter. The tertiary processed wire A-5 was annealed at 480° C. for an hour and then subjected to cold wiredrawing. Thus, the plastic-processed wire A of 4 mm in diameter was obtained.

Example 2 prepared combination-processed materials in wire form (hereinafter collectively referred to as combination-processed wires B) having compositions shown in Table 2 or 3: Nos. 501 to 528, Nos. 601 to 607, Nos. 701 to 708, and Nos. 801 to 805. Wires Nos. 501 to 528 belong to the fifth copper alloy material; wires Nos. 601 to 607 belong to the sixth copper alloy material; wires No. 701 to No. 708 belong to the seventh copper alloy material; wires Nos. 801 to 805 belong to the eighth copper alloy material.

The combination-processed wires Nos. 501 to 528, Nos. 601 to 607, Nos. 701 to 708, and Nos. 801 to 805 were each prepared as follows. First, a casting wire B-1 of 6 mm in diameter having the corresponding composition shown in Table 2 or 3 was subjected to continuous casting at a low speed (1 m/minute) with a casting apparatus including a melting furnace (ingoting ability: 60 kg) equipped with a horizontal continuous casting machine. Molding is continuously performed with graphite while additive elements were added as needed so as to give a predetermined composition. Then, the casting wire B-1 was subjected to cold wiredrawing to form a primary processed wire B-2 of 4.3 mm in diameter. This wiredrawing was performed through the two steps of: drawing the casting wire B-1 into an intermediate wire of 5 mm in diameter; and further drawing the intermediate wire into the primary processed wire B-2 of 4.3 mm in diameter. The primary processed wire B-2 was annealed at 480° C. for an hour and then subjected to cold wiredrawing. Thus, the combination-processed wire B of 4 mm in diameter was obtained.

Comparative Example 1 prepared wires Nos. 1001 to 1006 of 4 mm in diameter (hereinafter collectively referred to as first comparative example wires C) having compositions shown in Table 4 in the same manufacturing process as in the case of the plastic-processed wires A of Example 1. The first comparative example wires C were prepared for comparison with the first to fourth copper alloy materials. As for wire No. 1003, a large defect (crack) occurred in the course of forming the primary-processed wire A-3, and thus no intended wire C was obtained.

Comparative Example 2 prepared combination-processed wires Nos. 2001 to 2013 and Nos. 2501 to 2505 of 4 mm in diameter (hereinafter collectively referred to as second comparative example wires D) having compositions shown in Table 5 in the same manufacturing process as in the case of the combination-processed wires B of Example 2. The second comparative example wires D were prepared for comparison with the fifth to eighth copper alloy materials. Wires Nos. 2501 to 2505 contain the same elements as wires Nos. 501 to 505 respectively, except that crystal grain-refining elements Zr and P were not added. As for wires Nos. 2009 and 2011, large defects occurred in the course of forming the primary processed wires B-2. As for wires Nos. 2010, 2012, and 2502 to 2505, large defects occurred in the course of forming the casting wires B-1. Thus, second comparative example wires D for those numbers were not obtained. As for wires Nos. 2001, 2002, 2005, and 2013, although cracks occurred in their primary processed wires B-2, intended second comparative example wires D were obtained because the cracks were not so large.

The resulting wires A, B, C, and D were subjected to tension tests and bending tests for inspecting the mechanical properties as follows.

The tension test was performed to obtain the tensile strength (N/mm$^2$), elongation (%), and fatigue strength (N/mm$^2$) of the wires A, B, C, and D with an Amsler universal tester. The results are shown in Tables 6 to 10. On Nos. 1003, 2009, 2010, 2011, 2012, and 2502 to 2505, which did not achieve intended wires C and D, the tension test and the following tests were not performed.

For the bending test, each of wires A, B, C, and D extending in the vertical direction was fixed at the midpoint and was repeatedly subjected to several bending operations until the curved portion was cracked, and thus the durability to repetitive deformation was examined. The single bending operation was performed such that the upper portion from the fixed portion was bent in a horizontal direction at a bend radius of 6 mm, then restored to the vertical state, further bent in the reverse horizontal direction, and restored to the vertical state again. The results are shown in Tables 6 to 10.

In addition, wires A, B, C, and D were subjected to the following seawater resistance tests I to IV and the dezincification corrosion resistance test specified in ISO 6509 to examine the corrosion resistance and the seawater resistance.

In the seawater resistance tests I to IV, erosion-corrosion test was performed such that a test solution (30° C.) was jetted at a flow rate of 11 m/s onto test pieces of the wires A, B, C, and D from a nozzle with a bore of 1.9 mm in the direction perpendicular to the axis of the wires. After a predetermined time T had elapsed, corrosion weight loss ($mg/cm^2$) was measured. The test solution was: 3% salt solution for seawater resistance tests I and II; a mixed solution of $CuCl_2.H_2O$ (0.13 g/L) in 3% salt solution for seawater resistance test III; and 3% salt solution containing glass beads (5 vol. %) with a average diameter of 0.115 mm for seawater resistance test IV. The corrosion weight loss was defined by the difference per square centimeter ($mg/cm^2$) between the weights of the test piece before test and after jetting the test solution onto the test piece for a time T. The jetting time was: 96 hours for seawater resistance tests I and III; 960 hours for seawater resistance test II; and 24 hours for seawater resistance test IV. The results of seawater resistance tests I to IV are shown in Tables 6 to 10.

In the dezincification corrosion resistance test of ISO 6509, test pieces of the wires A, B, C, and D were each fixed to a phenol resin such that the exposed surfaces of the test pieces were perpendicular to the direction of expansion and contraction, and the surfaces of the test pieces were ground with emery papers of up to #1200. Then, test pieces were ultrasonic-cleaned in pure water, following by drying. The thus obtained corroded test pieces were immersed in 1.0% copper (II) chloride dihydrate ($CuCl_2.2H_2O$) solution and allowed to stand at 75° C. for 24 hours. Then, the test pieces were taken out of the solution and the maximum depth of dezincification corrosion (μm) was measured. The results are shown in Tables 6 to 10.

The phase structures of the wires A, B, C, and D were subjected to image analysis to measure the area ratios (%) of the α, γ, and δ phases. Specifically, a phase structure image taken at a magnification of 200 times by an optical microscope was binarized with an image processing software program "WinROOF" and the area ratio of each phase was determined. The area ratio of each phase was measured in three views and the average was defined as the area ratio of the corresponding phase. The results, which are shown in Tables 1 to 4, suggest that the phase structure described above is required for the characteristics described above.

The average grain sizes (μm) of the wires B and D after melt-solidification were measured. Specifically, the cut surface of the casting wire B-1 was etched with nitric acid, and the average grain size of the macroscopic structure appearing at the etched surface was measured at a magnification of 7.5 times. This measurement was performed in accordance with the comparison method for estimating average grain size of copper elongation products specified in JIS H0501. More specifically, for the crystal grains of about 0.5 mm or more in diameter, the cut surface was etched with nitric acid and observed at a magnification of 7.5 times; for the crystal grains of about less than 0.1 mm in diameter, the cut surface was etched with a mixed solution of hydrogen peroxide solution and ammonia water and observed at a magnification of 75 time with an optical microscope. The results are shown in Tables 7, 8, and 10.

As shown in Tables 6 to 10, it has been shown that the first to eighth copper alloy materials, namely, wires A and B, have superior corrosion resistance and seawater resistance to the comparative example wires C and D, and besides, have superior mechanical properties, such as tensile strength, and durability to repetitive deformation. In the fifth to eighth copper alloy materials, the crystal grains are notably refined by adding Zr and P in combination. Consequently, the above characteristics were extremely increased. In particular, the effect of combined use of Zr and P in refining the crystal grains is clearly shown by comparing the average grain sizes of the combination-processed wires Nos. 501 to 505 with those of the second comparative example wires Nos. 2501 to 2505 containing the same constituent elements except Zr or P.

The wire drawability of wires A, B, D, and C was evaluated according to the following criteria. For wires A and C, when the primary processed wire A-3 (diameter: 9 mm) having no crack was obtained from the round bar A-2 (diameter: 12 mm) by a single wiredrawing operation (processing rate: about 44%), the wire drawability was determined to be good; when the primary processed wire A-3 having no crack could not be obtained by the single wiredrawing operation, but it was obtained by the wiredrawing (two operations) of Example 1 or Comparative Example 1, the wire drawability was determined to be ordinary; when the primary processed wire A-3 having no crack could not be obtained by the wiredrawing (two operations) of Example 1 or Comparative Example 1, the wire drawability was determined to be poor. For wires B and D, when the primary processed wire B-2 (diameter: 4.3 mm) having no crack was obtained from the casting wire B-1 (diameter: 6 mm) by a single wiredrawing operation (processing rate: about 49%), the wire drawability was determined to be good; when the primary processed wire B-2 having no crack could not be obtained by the single wiredrawing operation, but it was obtained by the wiredrawing (two operations) of Example 2 or Comparative Example 2, the wire drawability was determined to be ordinary; when the primary processed wire B-2 having no crack could not be obtained by the wiredrawing (two operations) of Example 2 or Comparative Example 2, the wire drawability was determined to be poor. The results are shown in Tables 6 to 10. In these tables, the wires having good drawability are shown as "Good"; the wires having ordinary wire drawability are shown as "fair"; the wire having poor wire drawability are shown as "Poor".

The castability of wires B and D was evaluated by a castability test. In the castability test, the casting wire B-1 was subjected to continuous casting under the same conditions as in Example 2 or Comparative Example 2 in three stages at cast speeds of 3 m/minute, 1.8 m/minute, and 1 m/minute. Whether the castability is good or not was determined depending on the casting speed at which the casting wire B-1 having no defect was obtained. The results are shown in Tables 7, 8, and 10. In the tables, when the casting wire B-1 having no defect was obtained by high-speed casting at 3 m/minute, the castability was determined to be excellent and is shown as "Excellent"; when the casting wire B-1 having no defect could not be obtained by high-speed casting, but it was obtained by middle-speed casting at 1.8 m/minute, the castability was determined to be good and is shown as "Good"; when the casting wire B-1 having no defect could not be obtained by high-speed casting or middle speed casting, but it was able to be obtained by low-speed casting at 1 m/minute, the castability was determined to be ordinary and is shown as "Fair"; when the casting wire B-1 having no defect could not be obtained even by low-speed casting (1 m/minute), the castability was determined to be poor and is shown as "Poor". The wired whose castability was determined to be poor (shown as "Poor") were not subjected to the castability test, but the castability was evaluated depending on the casting states in the process for making wires B and D in Example 2 or Comparative Example 2. Specifically, when the casting wire B-1 having no defect could not be obtained in the casting step (low-speed casting at 1 m/minute) of the process, the castability was determined to be poor without conducting the evaluation test.

As shown in Tables 6 to 10, it has been shown that the first to eighth copper alloy materials, namely, wires A and B, have superior wire drawability to the comparative example wires C and D. It has also been shown that the fifth to eighth copper alloy materials or wires A have not only superior wire drawability but also superior castability due to refined crystal grains.

Example 3 prepared a square tube-like cultivation net 3 (see FIGS. 1 to 3) with a side of 9 m and a depth (length in the vertical direction) of 5 m by netting the plastic-processed wire A obtained in Example 1 or the combination-processed wire B obtained in Example 2 into a rhombically netted structure (mesh S: 40 mm). Specifically, plastic-processed wire No. 405 was netted into cultivation net No. 1, and combination-processed wires Nos. 520, 525, and No. 704 were netted into cultivation nets Nos. 2, 3, and 4, respectively, as shown in Table 11.

Comparative Example 3 prepared cultivation nets Nos. 5 and No. 6 having the same shape as in Example 3 by respectively netting the first comparative example wires Nos. 1004 and 1005, as shown in Table 11.

Fish preserves as shown in FIG. 1 were constructed using cultivation nets Nos. 1 to 6. For each sample number of cultivation nets, two fish preserves (cultivation nets) were each prepared for culturing yellowtail or salmon. The reinforcing frame 4 (see FIGS. 1 and 4) of about 2000 kg was attached to each of cultivation nets Nos. 1 to 6 in such a manner that the clearance L at the entwined portions 6a was about 2 mm on average.

Then, migratory fish (yellowtail and salmon) were cultured using each fish preserve in a practical fish farm. When a year had elapsed after the start of the cultivation, the maximum wire thickness loss (mm) of cultivation nets Nos. 1 to 6 was determined. The wire thickness loss was measured at arbitrarily selected 10 points (measurement points) in each section of the corner (corner in draft region) of the periphery 3a in the draft region (region from 10 cm to 30 cm under the surface of the sea), the region other than the corner of the periphery 3a in the draft region (periphery in draft region), the periphery 3a (region of the periphery lower than the draft region), and the bottom 3b. The maximum in the obtained values was defined as the maximum wire thickness loss. The results are shown in Table 11. The wire thickness loss was calculated by subtracting the thickness of each measurement point after a year from the initial thickness (4 mm) of the measurement point.

As clearly shown in Table 11, cultivation nets Nos. 1 to 4 of Example 3 exhibited a much lower wire thickness loss at each measurement point than cultivation nets Nos. 5 and 6 of Comparative Example 3, in spite of a short period of testing time (one year). Thus, it has been shown that cultivation nets of Example 3 have superior durability. In addition, the adhesion of marine organisms, such as ("acorn shells"), to cultivation nets Nos. 1 to 6 was hardly found even after a year had elapsed.

TABLE 1

| | Wire No. | Alloy composition | | | | | | | | | | Compositional value | | Phase structure Area ratio (%) | |
|---|---|---|---|---|---|---|---|---|---|---|---|---|---|---|---|
| | | Constituent element (mass %) | | | | | | | | | | | | | |
| | | Cu | Zn | P | Sn | Al | As | Sb | Mn | Si | Ni | Mg | Y1 to Y8 | Y9 | α + γ + δ | γ + δ |
| Example 1 | 101 | 81.5 | 17.7 | | 0.8 | | | | | | | | 81.1 | 4.1 | 100 | 0 |
| | 102 | 90.1 | 8.5 | | 1.4 | | | | | | | | 89.4 | 4.0 | 100 | 0 |
| | 103 | 66.2 | 32.5 | | 1.3 | | | | | | | | 65.6 | 2.7 | 100 | 2.0 |
| | 104 | 65.3 | 33.6 | | 1.1 | | | | | | | | 64.8 | 2.8 | 99.0 | 1.0 |
| | 105 | 66.4 | 32.6 | 0.05 | 1.0 | | | | | | | | 65.8 | 3.0 | 100 | 0.1 |
| | 106 | 64.9 | 34.1 | 0.10 | 0.9 | | | | | | | | 64.2 | 3.0 | 100 | 0.5 |
| | 107 | 65.0 | 33.1 | 0.10 | 1.8 | | | | | | | | 63.8 | 2.1 | 100 | 7.0 |
| | 108 | 65.0 | 33.4 | 0.06 | 1.5 | | | | | | | | 64.1 | 2.4 | 100 | 4.5 |
| | 201 | 62.6 | 36.5 | | 0.8 | | 0.08 | | | | | | 62.2 | 3.0 | 98.0 | 0.5 |
| | 202 | 63.4 | 36.0 | | 0.5 | | 0.07 | | | | | | 63.1 | 3.3 | 99.5 | 0 |
| | 203 | 64.3 | 34.4 | | 1.2 | | 0.08 | | | | | | 63.7 | 2.7 | 100 | 3.5 |
| | 204 | 65.5 | 33.7 | | 0.8 | 0.04 | | | | | | | 65.1 | 3.1 | 100 | 0 |
| | 205 | 65.5 | 33.7 | | 0.8 | | | | | | | 0.02 | 65.1 | 3.1 | 100 | 0 |
| | 206 | 65.3 | 33.6 | | 1.0 | 0.10 | 0.03 | | | | | | 64.7 | 2.9 | 100 | 0.5 |
| | 301 | 66.0 | 31.9 | | 1.1 | | | | 0.7 | 0.3 | | | 65.8 | 2.9 | 100 | 2.0 |
| | 302 | 66.5 | 32.2 | | 1.1 | | | | | 0.2 | | | 65.3 | 2.9 | 100 | 1.5 |
| | 303 | 65.5 | 33.4 | | 1.0 | 0.2 | | | | | | | 64.7 | 2.9 | 100 | 1.0 |
| | 304 | 64.2 | 33.5 | | 0.9 | | | | 1.1 | 0.3 | | | 64.9 | 3.0 | 100 | 0 |
| | 305 | 67.4 | 30.7 | 0.05 | 1.2 | 0.7 | | | | | | | 65.4 | 2.8 | 100 | 1.0 |
| | 401 | 66.8 | 31.7 | | 1.0 | 0.4 | | 0.07 | | | | | 65.5 | 3.0 | 100 | 0 |
| | 402 | 69.1 | 28.4 | 0.04 | 1.0 | 1.4 | | | | | | 0.05 | 66.0 | 3.1 | 100 | 0 |
| | 403 | 70.5 | 26.9 | | 1.3 | | 0.08 | 0.03 | 1.2 | | | | 65.6 | 2.9 | 100 | 4.0 |
| | 404 | 66.8 | 31.7 | | 1.0 | | | 0.06 | 0.4 | | | | 64.9 | 3.0 | 100 | 0.5 |
| | 405 | 65.8 | 33.0 | | 1.1 | | | 0.06 | | 0.03 | | | 65.3 | 2.8 | 100 | 0.3 |

TABLE 2

| | Wire No. | Constituent element (mass %) | | | | | | Compositional value | | content ratio | | | Phase structure Area ratio (%) | |
|---|---|---|---|---|---|---|---|---|---|---|---|---|---|---|
| | | Cu | Zn | Zr | P | Sn | impurity | Y1 to Y8 | Y9 | Z1 | Z2 | Z3 | α + γ + δ | γ + δ |
| Example 2 | 501 | 68.8 | 29.9 | 0.0080 | 0.060 | 1.20 | | 68.0 | 2.9 | 7.5 | 150.0 | 20.0 | 100 | 0.5 |
| | 502 | 72.6 | 25.9 | 0.0090 | 0.070 | 1.40 | | 71.7 | 3.0 | 7.8 | 155.6 | 20.0 | 100 | 0 |
| | 503 | 75.8 | 22.1 | 0.0090 | 0.050 | 2.00 | | 74.7 | 2.5 | 5.6 | 222.2 | 40.0 | 100 | 0.3 |
| | 504 | 80.5 | 17.0 | 0.0150 | 0.080 | 2.40 | | 79.1 | 2.4 | 5.3 | 160.0 | 30.0 | 100 | 0 |
| | 505 | 90.2 | 6.2 | 0.0230 | 0.090 | 3.50 | | 88.2 | 1.9 | 3.9 | 152.2 | 38.9 | 100 | 0 |
| | 506 | 66.2 | 32.7 | 0.0053 | 0.060 | 1.00 | | 65.5 | 3.0 | 11.3 | 188.7 | 16.7 | 100 | 0 |
| | 507 | 66.0 | 32.9 | 0.0015 | 0.060 | 1.00 | | 65.3 | 3.0 | 40.0 | 666.7 | 16.7 | 100 | 0.3 |
| | 508 | 66.5 | 32.3 | 0.0090 | 0.045 | 1.10 | | 65.8 | 2.9 | 5.0 | 122.2 | 24.4 | 100 | 0 |
| | 509 | 66.8 | 32.0 | 0.0120 | 0.070 | 1.10 | | 66.0 | 2.9 | 5.8 | 91.7 | 15.7 | 100 | 0 |
| | 510 | 66.3 | 32.6 | 0.0270 | 0.060 | 1.00 | | 65.6 | 3.0 | 2.2 | 37.0 | 16.7 | 100 | 0 |
| | 511 | 66.3 | 32.6 | 0.0380 | 0.080 | 1.00 | | 65.6 | 3.0 | 2.1 | 26.3 | 12.5 | 100 | 0 |
| | 512 | 74.1 | 24.6 | 0.0180 | 0.070 | 1.20 | | 73.3 | 3.2 | 3.9 | 66.7 | 17.1 | 100 | 0 |
| | 513 | 63.2 | 36.0 | 0.0150 | 0.060 | 0.70 | | 62.7 | 3.1 | 4.0 | 46.7 | 11.7 | 99.0 | 0.5 |
| | 514 | 62.7 | 36.6 | 0.0160 | 0.060 | 0.60 | | 62.2 | 3.2 | 3.8 | 37.5 | 10.0 | 97.5 | 1.0 |
| | 515 | 66.0 | 33.9 | 0.0120 | 0.050 | 0.07 | | 65.8 | 3.9 | 4.2 | 5.8 | 1.4 | 100 | 0 |
| | 516 | 66.5 | 33.0 | 0.0090 | 0.060 | 0.45 | | 66.1 | 3.5 | 6.7 | 50.0 | 7.5 | 100 | 0 |
| | 517 | 66.0 | 33.2 | 0.0140 | 0.050 | 0.70 | | 65.5 | 3.3 | 3.6 | 50.0 | 14.0 | 100 | 0 |
| | 518 | 76.0 | 20.5 | 0.0090 | 0.050 | 3.40 | | 74.2 | 1.2 | 5.6 | 377.8 | 68.0 | 100 | 4.5 |
| | 519 | 68.8 | 29.8 | 0.0180 | 0.180 | 1.20 | | 67.7 | 2.9 | 10.0 | 66.7 | 6.7 | 100 | 0.5 |
| | 520 | 73.0 | 25.6 | 0.0090 | 0.045 | 1.30 | | 72.2 | 3.1 | 5.0 | 144.4 | 28.9 | 100 | 0 |
| | 521 | 73.5 | 24.9 | 0.0130 | 0.060 | 1.50 | | 72.6 | 2.9 | 4.6 | 115.4 | 25.0 | 100 | 0.5 |
| | 522 | 67.5 | 30.4 | 0.0090 | 0.070 | 2.00 | | 66.3 | 2.1 | 7.8 | 222.2 | 28.6 | 100 | 8.0 |
| | 523 | 66.5 | 32.0 | 0.0080 | 0.080 | 1.40 | | 65.6 | 2.6 | 10.0 | 175.0 | 17.5 | 100 | 4.5 |
| | 524 | 72.2 | 26.4 | 0.0150 | 0.070 | 1.20 | Fe: 0.07 | 71.5 | 3.1 | 4.7 | 80.0 | 17.1 | 100 | 0 |

TABLE 3

| | Wire No. | Alloy composition Constituent element (mass %) | | | | | | | | | | |
|---|---|---|---|---|---|---|---|---|---|---|---|---|
| | | Cu | Zn | Zr | P | Sn | Al | As | Sb | Mn | Si | Ni |
| Example 2 | 525 | 72.0 | 26.7 | 0.015 | 0.070 | 1.2 | | | | | | |
| | 526 | 71.0 | 27.8 | 0.015 | 0.070 | 1.1 | | | | | | |
| | 527 | 66.0 | 32.9 | 0.035 | 0.022 | 1.0 | | | | | | |
| | 528 | 66.0 | 32.8 | 0.004 | 0.170 | 1.0 | | | | | | |
| | 601 | 66.0 | 32.9 | 0.016 | 0.015 | 1.0 | | | 0.02 | | | |
| | 602 | 65.8 | 33.1 | 0.009 | 0.060 | 0.9 | 0.10 | | | | | |
| | 603 | 66.5 | 32.3 | 0.013 | 0.028 | 1.1 | | | 0.02 | | | |
| | 604 | 66.0 | 32.8 | 0.009 | 0.070 | 1.1 | | | 0.06 | | | |
| | 605 | 66.2 | 32.8 | 0.009 | 0.120 | 0.8 | | | | | | |
| | 606 | 72.8 | 25.7 | 0.013 | 0.090 | 1.4 | | 0.04 | | | | |
| | 607 | 74.2 | 24.5 | 0.019 | 0.060 | 1.2 | | | | | | |
| | 701 | 80.3 | 17.1 | 0.016 | 0.070 | 2.4 | 0.14 | | | | 0.15 | |
| | 702 | 68.0 | 30.7 | 0.009 | 0.080 | 1.1 | | | | | | |
| | 703 | 67.2 | 30.7 | 0.015 | 0.050 | 1.0 | | | | 0.70 | 0.35 | |
| | 704 | 72.5 | 25.8 | 0.009 | 0.060 | 1.3 | 0.31 | | | | | |
| | 705 | 68.4 | 29.8 | 0.012 | 0.070 | 1.2 | 0.52 | | | | | |
| | 706 | 65.5 | 31.9 | 0.010 | 0.050 | 0.9 | | | | 1.20 | 0.40 | |
| | 707 | 74.0 | 24.5 | 0.015 | 0.080 | 1.2 | | | | 0.18 | 0.07 | |
| | 708 | 71.5 | 27.0 | 0.015 | 0.080 | 1.2 | | | | | 0.17 | |
| | 801 | 67.3 | 31.3 | 0.009 | 0.060 | 1.2 | 0.08 | | 0.03 | | | |
| | 802 | 67.4 | 31.3 | 0.012 | 0.070 | 1.0 | 0.20 | 0.06 | | | | |
| | 803 | 69.5 | 28.2 | 0.009 | 0.050 | 1.0 | 1.20 | | | | | |
| | 804 | 72.0 | 25.6 | 0.011 | 0.080 | 1.1 | | 0.05 | 0.03 | | 1.10 | |
| | 805 | 67.0 | 31.7 | 0.012 | 0.060 | 1.0 | | | 0.06 | | 0.20 | |

| | Constituent element (mass %) | | Compositional value | | content ratio | | | Phase structure Area ratio (%) | |
|---|---|---|---|---|---|---|---|---|---|
| | Mg | impurity | Y1 to Y8 | Y9 | Z1 | Z2 | Z3 | α + γ + δ | γ + δ |
| Example 2 | | Fe: 0.03 | 71.2 | 3.1 | 4.7 | 80.0 | 17.1 | 100 | 0 |
| | | Ni: 0.03 | 70.3 | 3.2 | 4.7 | 73.3 | 15.7 | 100 | 0 |
| | | | 65.4 | 3.0 | 0.6 | 28.6 | 45.5 | 100 | 0 |
| | | | 65.0 | 3.0 | 42.5 | 250.0 | 5.9 | 100 | 0 |
| | | | 65.4 | 3.0 | 0.9 | 62.5 | 66.7 | 100 | 0.3 |

TABLE 3-continued

|  |  |  |  |  |  |  |  |
|---|---|---|---|---|---|---|---|
|  |  | 65.1 | 3.0 | 6.7 | 100.0 | 15.0 | 100 | 0 |
|  |  | 65.9 | 2.9 | 2.2 | 84.6 | 39.3 | 100 | 0 |
|  | 0.110 | 65.2 | 2.9 | 7.8 | 122.2 | 15.7 | 100 | 1.0 |
|  |  | 65.4 | 3.2 | 13.3 | 88.9 | 6.7 | 100 | 0 |
|  |  | 71.8 | 3.0 | 6.9 | 107.7 | 15.6 | 100 | 0 |
|  | 0.008 | 73.4 | 3.3 | 3.2 | 63.2 | 20.0 | 100 | 0 |
|  |  | 78.6 | 2.4 | 4.4 | 150.0 | 34.3 | 100 | 0.5 |
|  |  | 66.7 | 3.0 | 8.9 | 122.2 | 13.8 | 100 | 0 |
|  |  | 66.7 | 3.0 | 3.3 | 66.7 | 20.0 | 100 | 0 |
|  |  | 71.1 | 3.1 | 6.7 | 144.4 | 21.7 | 100 | 0 |
|  |  | 66.7 | 2.9 | 5.8 | 100.0 | 17.1 | 100 | 0 |
|  |  | 65.9 | 3.0 | 5.0 | 90.0 | 18.0 | 100 | 0.3 |
|  |  | 73.3 | 3.2 | 5.3 | 80.0 | 15.0 | 100 | 0 |
|  |  | 70.9 | 3.1 | 5.3 | 80.0 | 15.0 | 100 | 0 |
|  |  | 66.4 | 2.8 | 6.7 | 133.3 | 20.0 | 100 | 1.5 |
|  |  | 66.3 | 3.0 | 5.8 | 83.3 | 14.3 | 100 | 0 |
|  | 0.050 | 66.7 | 3.2 | 5.6 | 111.1 | 20.0 | 100 | 0 |
|  |  | 67.3 | 3.2 | 7.3 | 100.0 | 13.8 | 100 | 0 |
|  |  | 65.6 | 3.0 | 5.0 | 83.3 | 16.7 | 100 | 0 |

TABLE 4

|  |  | Alloy composition | | | | | Compositional value | | Phase structure Area ratio (%) | |
|---|---|---|---|---|---|---|---|---|---|---|
|  | Wire | Constituent element (mass %) | | | | | | | | |
|  | No. | Cu | Zn | P | Sn | Sb | Y1 to Y8 | Y9 | α + γ + δ | γ + δ |
| Comparative example 1 | 1001 | 61.4 | 37.6 |  | 0.900 | 0.06 | 60.9 | 2.8 | 94.0 | 1.0 |
|  | 1002 | 91.8 | 7.2 |  | 0.900 | 0.08 | 91.3 | 4.6 | 100 | 0 |
|  | 1003 | 65.5 | 32.0 | 0.05 | 2.500 |  | 64.1 | 1.4 | 100 | 12.0 |
|  | 1004 | 79.8 | 20.2 |  | 0.005 |  | 79.8 | 4.8 | 100 | 0 |
|  | 1005 | 65.1 | 34.9 |  | 0.007 |  | 65.1 | 3.9 | 100 | 0 |
|  | 1006 | 65.2 | 34.8 |  | 0.005 | 0.01 | 65.2 | 3.9 | 100 | 0 |

TABLE 5

|  |  | Alloy composition | | | | | | | | Compositional value | | content ratio | | | Phase structure Area ratio (%) | |
|---|---|---|---|---|---|---|---|---|---|---|---|---|---|---|---|---|
|  |  | Constituent element (mass %) | | | | | | | | | | | | | | |
|  | Wire No. | Cu | Zn | Zr | P | Sn | Sb | Ni | impurity | Y1 to Y8 | Y9 | Z1 | Z2 | Z3 | α + γ + δ | γ + δ |
| Comparative example 2 | 2001 | 65.5 | 33.4 | 0.0004 | 0.060 | 1.000 |  |  |  | 64.8 | 2.9 | 150.0 | 2500.0 | 16.7 | 99.7 | 1.0 |
|  | 2002 | 66.0 | 33.0 | 0.0180 | 0.008 | 1.000 | 0.02 |  |  | 65.5 | 3.0 | 0.4 | 55.6 | 125.0 | 99.8 | 0 |
|  | 2003 | 65.7 | 33.1 | 0.0750 | 0.120 | 1.000 |  |  |  | 64.8 | 2.9 | 1.6 | 13.3 | 8.3 | 100 | 1.0 |
|  | 2004 | 62.0 | 37.2 | 0.0160 | 0.060 | 0.700 |  |  |  | 61.5 | 3.0 | 3.8 | 43.8 | 11.7 | 96.0 | 1.0 |
|  | 2005 | 61.2 | 38.0 | 0.0150 | 0.070 | 0.700 |  |  |  | 60.6 | 3.0 | 4.7 | 46.7 | 10.0 | 92.0 | 2.0 |
|  | 2006 | 64.8 | 35.1 | 0.0150 | 0.060 | 0.005 |  |  |  | 64.6 | 3.9 | 4.0 | 0.3 | 0.1 | 100 | 0 |
|  | 2007 | 91.5 | 5.6 | 0.0180 | 0.100 | 2.800 |  |  |  | 89.8 | 2.7 | 5.6 | 155.6 | 28.0 | 100 | 0 |
|  | 2008 | 90.6 | 8.8 | 0.0150 | 0.060 | 0.500 |  |  |  | 90.2 | 4.9 | 4.0 | 33.3 | 8.3 | 100 | 0 |
|  | 2009 | 75.8 | 19.8 | 0.0090 | 0.050 | 4.300 |  |  |  | 73.5 | 0.2 | 5.6 | 477.8 | 86.0 | 100 | 9.0 |
|  | 2010 | 68.8 | 29.7 | 0.0180 | 0.280 | 1.200 |  |  |  | 67.4 | 2.9 | 15.6 | 66.7 | 4.3 | 100 | 1.0 |
|  | 2011 | 68.0 | 29.3 | 0.0090 | 0.050 | 2.600 |  |  |  | 66.6 | 1.5 | 5.6 | 288.9 | 52.0 | 100 | 13.0 |
|  | 2012 | 73.6 | 24.5 | 0.0150 | 0.070 | 1.200 |  | 0.6 |  | 73.7 | 3.2 | 4.7 | 80.0 | 17.1 | 100 | 0 |
|  | 2013 | 70.8 | 27.4 | 0.0150 | 0.080 | 1.200 |  |  | Fe: 0.55 | 70.8 | 3.0 | 5.3 | 80.0 | 15.0 | 100 | 0 |
|  | 2501 | 68.8 | 29.9 |  | 0.060 | 1.200 |  |  |  | 68.0 | 2.9 |  |  |  | 100 | 0.5 |
|  | 2502 | 72.6 | 25.9 |  | 0.070 | 1.400 |  |  |  | 71.7 | 3.0 |  |  |  | 100 | 0 |
|  | 2503 | 75.8 | 22.2 |  |  | 2.000 |  |  |  | 74.8 | 2.5 |  |  |  | 100 | 0.1 |
|  | 2504 | 80.5 | 17.0 |  | 0.080 | 2.400 |  |  |  | 79.1 | 2.4 |  |  |  | 100 | 0 |
|  | 2505 | 90.2 | 6.2 |  | 0.090 | 3.500 |  |  |  | 88.2 | 1.9 |  |  |  | 100 | 0 |

TABLE 6

|  | wire No. | maximum depth of corrosion (μm) | corrosion weight loss (mg/cm$^2$) erosion-corrosion test | | | | wire drawability | tensile strength (N/mm$^2$) | elongation (%) | fatigue strength (N/mm$^2$) | number of bending sequences |
|---|---|---|---|---|---|---|---|---|---|---|---|
|  |  |  | I | II | III | IV |  |  |  |  |  |
| Example 1 | 101 | 20 | 25 | 140 | 65 | 310 |  | 372 | 17 | 152 | >5 |
|  | 102 | ≦10 | 22 | 114 | 68 | 350 |  | 355 | 14 | 148 | >5 |
|  | 103 | 90 | 27 | 153 | 85 | 275 |  | 457 | 18 | 168 | >5 |

TABLE 6-continued

| wire No. | maximum depth of corrosion (μm) | corrosion weight loss (mg/cm²) erosion-corrosion test | | | | wire drawability | tensile strength (N/mm²) | elongation (%) | fatigue strength (N/mm²) | number of bending sequences |
|---|---|---|---|---|---|---|---|---|---|---|
| | | I | II | III | IV | | | | | |
| 104 | 130 | 29 | 180 | 92 | 335 | | 445 | 20 | 174 | >5 |
| 105 | ≦10 | 23 | 108 | 60 | 246 | Good | 436 | 22 | 170 | >5 |
| 106 | 20 | 26 | 110 | 68 | 273 | | 440 | 22 | 168 | >5 |
| 107 | 150 | 34 | 189 | 105 | 335 | Fair | 479 | 12 | | 2 |
| 108 | 40 | 26 | 118 | 65 | 256 | Fair | 468 | 14 | | 3 |
| 201 | 170 | 35 | 202 | 113 | 348 | | 450 | 15 | | 3 |
| 202 | 90 | 28 | 145 | 79 | 313 | | 437 | 21 | | 5 |
| 203 | 40 | 25 | 118 | 65 | 275 | Good | 456 | 17 | | 4 |
| 204 | ≦10 | 22 | 95 | 60 | 230 | Good | 431 | 23 | 174 | >5 |
| 205 | 70 | 32 | 145 | 90 | 325 | | 425 | 24 | 165 | >5 |
| 206 | ≦10 | 23 | 103 | 65 | 220 | Good | 439 | 22 | 165 | >5 |
| 301 | 20 | 27 | 112 | 65 | 195 | | 483 | 14 | | 3 |
| 302 | ≦10 | 24 | 110 | 63 | 220 | | 440 | 19 | | 5 |
| 303 | ≦10 | 26 | 112 | 66 | 245 | | 437 | 21 | 168 | >5 |
| 304 | 30 | 27 | 128 | 69 | 160 | | 525 | 14 | 188 | 3 |
| 305 | ≦10 | 24 | 102 | 60 | 210 | | 475 | 19 | 180 | >5 |
| 401 | ≦10 | 23 | 108 | 60 | 213 | | 446 | 22 | 174 | >5 |
| 402 | ≦10 | 23 | 103 | 62 | 188 | | 505 | 17 | 185 | 4 |
| 403 | 35 | 26 | 120 | 70 | 190 | | 508 | 16 | 185 | 3 |
| 404 | ≦10 | 27 | 112 | 68 | 210 | | 453 | 21 | 165 | >5 |
| 405 | ≦10 | 24 | 104 | 63 | 218 | | 435 | 22 | 172 | >5 |

TABLE 7

| | Wire No. | Average grain size (μm) | Maximum depth of corrosion (μm) | Corrosion weight loss (mg/cm²) Erosion-corrosion test | | | | Castability | Wire drawability | Tensile strength (N/mm²) | Elongation (%) | Fatigue strength (N/mm²) | Number of bending sequences |
|---|---|---|---|---|---|---|---|---|---|---|---|---|---|
| | | | | I | II | III | IV | | | | | | |
| Example 2 | 501 | 30 | ≦10 | 21 | 98 | 58 | 205 | Excellent | Good | 445 | 21 | 177 | >5 |
| | 502 | 25 | ≦10 | 19 | 93 | 55 | 192 | Excellent | Good | 438 | 22 | 174 | >5 |
| | 503 | 35 | ≦10 | 20 | 95 | 54 | 194 | Excellent | Good | 431 | 22 | 170 | >5 |
| | 504 | 65 | ≦10 | 20 | 94 | 58 | 228 | Good | Good | 430 | 20 | 166 | >5 |
| | 505 | 95 | ≦10 | 21 | 89 | 56 | 277 | Good | Good | 418 | 19 | 155 | >5 |
| | 506 | 50 | ≦10 | 24 | 116 | 66 | 245 | Excellent | Good | 436 | 23 | 168 | >5 |
| | 507 | 120 | ≦10 | 25 | 123 | 72 | 266 | Good | Good | 418 | 20 | 153 | >5 |
| | 508 | 30 | ≦10 | 24 | 105 | 61 | 228 | Excellent | Good | 446 | 23 | 180 | >5 |
| | 509 | 25 | ≦10 | 23 | 101 | 60 | 215 | Excellent | Good | 438 | 23 | 178 | >5 |
| | 510 | 50 | ≦10 | 24 | 107 | 62 | 235 | Excellent | Good | 438 | 22 | 172 | >5 |
| | 511 | 90 | ≦10 | 23 | 108 | 65 | 233 | Excellent | Good | 435 | 21 | 170 | >5 |
| | 512 | 30 | ≦10 | 23 | 102 | 62 | 226 | Excellent | Good | 420 | 24 | 175 | >5 |
| | 513 | 40 | 120 | 29 | 161 | 89 | 328 | | | 437 | 22 | 155 | 5 |
| | 514 | 55 | 190 | 34 | 211 | 115 | 372 | | | 440 | 19 | 153 | 4 |
| | 515 | 40 | ≦10 | 28 | 169 | 81 | 392 | | | 413 | 25 | 151 | >5 |
| | 516 | 35 | ≦10 | 27 | 139 | 70 | 301 | | | 420 | 25 | 160 | >5 |
| | 517 | 30 | ≦10 | 26 | 115 | 72 | 278 | | | 425 | 23 | 165 | >5 |
| | 518 | 35 | 30 | 22 | 99 | 58 | 183 | | Fair | 448 | 12 | 167 | 3 |
| | 519 | 90 | ≦10 | 21 | 98 | 59 | 196 | Fair | | 435 | 17 | | 4 |
| | 520 | 35 | ≦10 | 19 | 93 | 55 | 192 | Excellent | Good | 438 | 22 | 174 | >5 |
| | 521 | 25 | ≦10 | 19 | 89 | 53 | 182 | Excellent | Good | 428 | 20 | 180 | >5 |
| | 522 | 30 | 100 | 29 | 132 | 81 | 280 | | Fair | 451 | 11 | | 3 |
| | 523 | 25 | 40 | 25 | 111 | 65 | 213 | | Fair | 462 | 14 | | 3 |
| | 524 | 120 | ≦10 | 22 | 103 | 65 | 218 | Excellent | | 435 | 19 | 165 | >5 |

TABLE 8

| | Wire No. | Average grain size (μm) | Maximum depth of corrosion (μm) | Corrosion weight loss (mg/cm²) Erosion-corrosion test | | | | Castability | Wire drawability | Tensile strength (N/mm²) | Elongation (%) | Fatigue strength (N/mm²) | Number of bending sequences |
|---|---|---|---|---|---|---|---|---|---|---|---|---|---|
| | | | | I | II | III | IV | | | | | | |
| Example 2 | 525 | 40 | ≦10 | 22 | 102 | 61 | 215 | Excellent | | 442 | 21 | 170 | >5 |
| | 526 | 35 | ≦10 | 21 | 100 | 59 | 205 | Excellent | Good | 438 | 22 | 168 | >5 |
| | 527 | 180 | 40 | 26 | 128 | 74 | 285 | | | 422 | 21 | 150 | >5 |
| | 528 | 200 | 20 | 23 | 110 | 67 | 235 | | | 430 | 17 | 160 | 4 |
| | 601 | 120 | 40 | 26 | 135 | 74 | 285 | Good | Fair | 422 | 18 | 150 | 4 |
| | 602 | 25 | ≦10 | 23 | 107 | 66 | 243 | | | 435 | 25 | 173 | >5 |

TABLE 8-continued

| Wire No. | Average grain size (μm) | Maximum depth of corrosion (μm) | Corrosion weight loss (mg/cm²) Erosion-corrosion test | | | | Castability | Wire drawability | Tensile strength (N/mm²) | Elongation (%) | Fatigue strength (N/mm²) | Number of bending sequences |
| | | | I | II | III | IV | | | | | | |
|---|---|---|---|---|---|---|---|---|---|---|---|---|
| 603 | 70 | 20 | 23 | 110 | 67 | 235 | Excellent | Good | 443 | 21 | 163 | >5 |
| 604 | 30 | ≦10 | 24 | 108 | 62 | 222 | | | 442 | 23 | 175 | >5 |
| 605 | 25 | ≦10 | 24 | 107 | 69 | 228 | Excellent | Good | 430 | 24 | 168 | >5 |
| 606 | 30 | ≦10 | 18 | 88 | 54 | 190 | | | 442 | 23 | | >5 |
| 607 | 40 | ≦10 | 20 | 90 | 55 | 194 | | | 428 | 22 | | >5 |
| 701 | 70 | ≦10 | 19 | 90 | 57 | 208 | Excellent | Good | 433 | 21 | 160 | >5 |
| 702 | 30 | ≦10 | 23 | 102 | 62 | 200 | | | 446 | 22 | | >5 |
| 703 | 35 | ≦10 | 24 | 108 | 66 | 172 | | | 485 | 18 | 185 | 4 |
| 704 | 25 | ≦10 | 19 | 88 | 51 | 172 | Excellent | Good | 446 | 23 | 175 | >5 |
| 705 | 25 | ≦10 | 21 | 94 | 55 | 180 | Excellent | Good | 455 | 23 | 185 | >5 |
| 706 | 40 | ≦10 | 24 | 110 | 67 | 145 | | | 478 | 18 | 190 | 4 |
| 707 | 35 | ≦10 | 19 | 104 | 59 | 198 | | | 452 | 20 | 180 | >5 |
| 708 | 180 | ≦10 | 23 | 108 | 67 | 230 | Good | Fair | 438 | 18 | | 5 |
| 801 | 30 | ≦10 | 23 | 101 | 58 | 185 | Excellent | Good | 445 | 20 | 174 | >5 |
| 802 | 25 | ≦10 | 23 | 98 | 60 | 184 | | | 440 | 23 | | >5 |
| 803 | 25 | ≦10 | 21 | 99 | 55 | 152 | | | 465 | 20 | | >5 |
| 804 | 35 | ≦10 | 23 | 100 | 59 | 165 | | | 471 | 20 | | >5 |
| 805 | 35 | ≦10 | 22 | 105 | 60 | 198 | | | 450 | 22 | | >5 |

TABLE 9

| | Wire No. | Maximum depth of corrosion (μm) | Corrosion weight loss (mg/cm²) Erosion-corrosion test | | | | Wire drawability | Tensile strength (N/mm²) | Elongation (%) | Fatigue strength (N/mm²) | Number of bending sequences |
| | | | I | II | III | IV | | | | | |
|---|---|---|---|---|---|---|---|---|---|---|---|
| Comparative example 1 | 1001 | 400 | 51 | 330 | 164 | 535 | Fair | 488 | 11 | | 2 |
| | 1002 | ≦10 | 29 | 205 | 72 | 445 | | 340 | 16 | | >5 |
| | 1003 | | | | | | Poor | | | | |
| | 1004 | 140 | 34 | 235 | 95 | 495 | | 335 | 20 | 130 | >5 |
| | 1005 | 250 | 39 | 258 | 112 | 500 | | 398 | 22 | 142 | >5 |
| | 1006 | 240 | 38 | 260 | 113 | 493 | | 397 | 22 | 143 | >5 |

TABLE 10

| | Wire No. | Average grain size (μm) | Maximum depth of corrosion (μm) | Corrosion weight loss (mg/cm²) Erosion-corrosion test | | | | Castability | Wire drawability | Tensile strength (N/mm²) | Elongation (%) | Fatigue strength (N/mm²) | Number of bending sequences |
| | | | | I | II | III | IV | | | | | | |
|---|---|---|---|---|---|---|---|---|---|---|---|---|---|
| Comparative example 2 | 2001 | 800 | 90 | 28 | 145 | 90 | 345 | Fair | Poor | 399 | 15 | 135 | 3 |
| | 2002 | 700 | 90 | 27 | 153 | 80 | 320 | Fair | Poor | 405 | 16 | 138 | 3 |
| | 2003 | 200 | ≦10 | 24 | 110 | 64 | 240 | Good | Fair | 425 | 20 | 162 | 5 |
| | 2004 | 180 | 380 | 47 | 325 | 170 | 498 | | | 456 | 16 | 150 | 3 |
| | 2005 | 350 | 480 | 55 | 350 | 203 | 566 | | Poor | 478 | 11 | 148 | 2 |
| | 2006 | 40 | 20 | 33 | 216 | 94 | 495 | | | 410 | 25 | 150 | >5 |
| | 2007 | 250 | ≦10 | 25 | 126 | 68 | 402 | | | 375 | 17 | 140 | 5 |
| | 2008 | 350 | ≦10 | 26 | 168 | 75 | 456 | | | 335 | 15 | 133 | 4 |
| | 2009 | 40 | | | | | | | Poor | | | | |
| | 2010 | 150 | | | | | | Poor | | | | | |
| | 2011 | 25 | | | | | | | Poor | | | | |
| | 2012 | 400 | | | | | | Poor | | | | | |
| | 2013 | 300 | 30 | 27 | 113 | 82 | 215 | Fair | Poor | 470 | 14 | 160 | 3 |
| | 2501 | 1000 | 40 | 24 | 118 | 92 | 345 | Fair | Fair | 405 | 12 | 135 | 3 |
| | 2502 | 1200 | | | | | | Poor | | | | | |
| | 2503 | 1300 | | | | | | Poor | | | | | |
| | 2504 | 1500 | | | | | | Poor | | | | | |
| | 2505 | 1500 | | | | | | Poor | | | | | |

TABLE 11

|  | Cultivation net No. | Wire No. | Cultured fish | Wire thickness loss (mm) | | | |
|---|---|---|---|---|---|---|---|
|  |  |  |  | Corner in draft region | Periphery in draft region | Periphery | Bottom |
| Example 3 | 1 | 405 | Yellowtail | 0.44 | 0.36 | 0.09 | 0.57 |
|  |  |  | Salmon | 0.42 | 0.35 | 0.03 | 0.05 |
|  | 2 | 509 | Yellowtail | 0.39 | 0.34 | 0.08 | 0.53 |
|  |  |  | Salmon | 0.38 | 0.33 | 0.03 | 0.05 |
|  | 3 | 521 | Yellowtail | 0.36 | 0.3 | 0.06 | 0.49 |
|  |  |  | Salmon | 0.34 | 0.29 | 0.02 | 0.04 |
|  | 4 | 704 | Yellowtail | 0.37 | 0.32 | 0.07 | 0.45 |
|  |  |  | Salmon | 0.36 | 0.32 | 0.03 | 0.05 |
| Comparative example 3 | 5 | 1004 | Yellowtail | 0.8 | 0.62 | 0.25 | 1.35 |
|  |  |  | Salmon | 0.85 | 0.64 | 0.08 | 0.1 |
|  | 6 | 1005 | Yellowtail | 1.05 | 0.75 | 0.28 | 2.0 |
|  |  |  | Salmon | 0.99 | 0.77 | 0.12 | 0.15 |

The invention claimed is:

1. A copper alloy material in wire or bar form for forming a netted structure used in seawater under harsh conditions, wherein the netted structure is exposed to water or waves running at high speed and rubbing, and wherein the copper alloy material comprises a composition including:
    (a) 62 to 91 mass % of Cu;
    (b) 0.6 to 3 mass % of Sn;
    (c) one or more elements selected from the group consisting of 0.02 to 1.5 mass % of Al, and 0.02 to 1.9 mass % of Si; and
    (d) the balance being Zn, wherein the composition satisfies the relationship derived from the Cu content [Cu], and the Sn content [Sn], in terms of mass %,
    $62 \leq [Cu] - 0.5[Sn] \leq 90$, wherein the copper alloy material has a phase structure including an α phase, a γ phase, and a δ phase, and the total area ratio of the α, γ, and δ phases is 95 to 100%, and the copper alloy material forms an Al—Sn coating or a Si—Sn coating when in seawater.

2. The copper alloy material according to claim 1, wherein the composition further contains one or more elements X1 selected from the group consisting of 0.02 to 0.25 mass % of As, 0.02 to 0.25 mass % of Sb, 0.001 to 0.2 mass % of Mg, and 0.01 to 0.25 mass % of P, and the composition satisfies the relationship derived from the Cu content [Cu], the Sn content [Sn], the Al content [Al], the Si content [Si], the P content [P], and the X1 total content [X1] except content [P] in terms of mass %, $62 \leq [Cu] - 0.5[Sn] - 3[P] - 0.5[X1] - 3.5[Si] - 1.8[Al] \leq 90$.

3. The copper alloy material according to claim 1, wherein the composition further contains one or more elements selected from the group consisting of 0.05 to 1.5 mass % of Mn, and 0.005 to 0.5 mass % of Ni, and the composition satisfies the relationship derived from the Cu content [Cu], the Sn content [Sn], the Al content [Al], the Mn content [Mn], the Si content [Si], and the Ni content [Ni] in terms of mass %, $62 \leq [Cu] - 0.5[Sn] - 3.5[Si] - 1.8[Al] + [Mn] + [Ni] \leq 90$.

4. The copper alloy material according to claim 2, wherein the composition further contains one or more elements selected from the group consisting of 0.05 to 1.5 mass % of Mn, and 0.005 to 0.5 mass % of Ni, and the composition satisfies the relationship derived from the Cu content [Cu], the Sn content [Sn], the P content [P], the X1 total content [X1] except content [P], the Al content [Al], the Mn content [Mn], the Si content [Si], and the Ni content [Ni] in terms of mass %, $62 \leq [Cu] - 0.5[Sn] - 3[P] - 0.5[X1] - 3.5[Si] - 1.8[Al] + [Mn] + [Ni] \leq 90$.

5. The copper alloy material according to claim 1, wherein the phase structure has a total area ratio of the γ and δ phases of 10% or less.

6. The copper alloy material according to claim 5, wherein the Cu content [Cu] and the Sn content [Sn] satisfy the relationship $1 \leq 0.06[Cu] - [Sn] \leq 4.5$ in terms of mass %.

7. A copper alloy material in wire or bar form for forming a netted structure used in seawater, the copper alloy material comprising a composition containing:
    (a) 62 to 91 mass % of Cu;
    (b) 0.6 to 3 mass % of Sn;
    (c) 0.0008 to 0.045 mass % of Zr;
    (d) 0.01 to 0.25 mass % of P; and
    (e) the balance being Zn, wherein the composition satisfies the relationship derived from the Cu content [Cu], Sn content [Sn], and P content [P] in terms of mass %,
    $62 \leq [Cu] - 0.5[Sn] - 3[P] \leq 90$, wherein the copper alloy material has a phase structure including an α phase, a γ phase, and a δ phase, wherein the total area ratio of the α, γ, and δ phases is 95 to 100%, and the average grain size is 0.2 mm or less after melt-solidification.

8. The copper alloy material according to claim 7, wherein the composition further contains at least one element X3 selected from the group consisting of 0.02 to 0.25 mass % of As, 0.02 to 0.25 mass % of Sb, and 0.001 to 0.2 mass % of Mg, and the composition satisfies the relationship derived from the Cu content [Cu], Sn content [Sn], P content [P], and X3 total content [X3] in terms of mass %: $62 \leq [Cu] - 0.5[Sn] - 3[P] - 0.5[X3] \leq 90$, and wherein the total area ratio of the α, γ, δ phases is 95 to 100% and the average grain size is 0.2 mm or less after melt-solidification.

9. The copper alloy material according to claim 7, wherein the composition further contains at least one element X4 selected from the group consisting of 0.02 to 1.5 mass % of Al, 0.05 to 1.5 mass % of Mn, 0.02 to 1.9 mass % of Si, and 0.005 to 0.5 mass % of Ni, and the composition satisfies the relationship derived from the Cu content [Cu], Sn content [Sn], P content [P], Al content [Al], Mn content [Mn], Si content [Si], and Ni content [Ni] in terms of mass %: $62 \leq [Cu] - 0.5[Sn] - 3[P] - 3.5[Si] - 1.8[Al] + [Mn] + [Ni] \leq 90$, and wherein the total area ratio of the α, γ, δ phases is 95 to 100% and the average grain size is 0.2 mm or less after melt-solidification.

10. The copper alloy material according to claim 8, wherein the composition further contains at least one element X4 selected from the group consisting of 0.02 to 1.5 mass % of Al, 0.05 to 1.5 mass % of Mn, 0.02 to 1.9 mass % of Si, and 0.005 to 0.5 mass % of Ni, and the composition satisfies the relationship derived from the Cu content [Cu], Sn content

[Sn], P content [P], X3 total content [X3], Al content [Al], Mn content [Mn], Si content [Si], and Ni content [Ni] in terms of mass %: $62 \leq [Cu]-0.5[Sn]-3[P]-0.5[X3]-3.5[Si]-1.8[Al]+[Mn]+[Ni] \leq 90$, and wherein the total area ratio of the α, γ, δ phases is 95 to 100% and the average grain size is 0.2 mm or less after melt-solidification.

11. The copper alloy material according to claim 7, wherein the Sn content [Sn], Zr content [Zr], and P content [P] of the composition satisfy the relationships $0.5 \leq [P]/[Zr] \leq 150$, $1 \leq [Sn]/[Zr] \leq 3000$, and $0.2 \leq [Sn]/[P] \leq 250$ in terms of mass %.

12. The copper alloy material according to claim 7, wherein the phase structure has a total area ratio of the γ and δ phases of 10% or less.

13. The copper alloy material according to claim 12, the Cu content [Cu] and Sn content [Sn] of the composition satisfy the relationship $1 \leq 0.06[Cu]-[Sn] \leq 4.5$ in terms of mass %.

14. The copper alloy material according to claim 11, wherein the primary crystal in melt-solidification is in the α phase.

15. The copper alloy material according to claim 7, wherein the composition contains an inevitable impurity being Fe, or Ni, or Fe and Ni, and the contents of inevitable impurities Fe and Ni are each 0.5 mass % or less.

16. The copper alloy material according to claim 11, wherein the copper alloy material is a cast-processed wire or bar, or a combination-processed wire or bar produced by subjecting the cast-processed wire or bar to plastic processing.

17. A method for manufacturing the copper alloy material in wire or bar form set forth in claim 7, the method comprising a casting step in which Zr is added in a form of a copper alloy containing Zr immediately before pouring, thus preventing the addition of an oxide, or a sulfide of Zr, or an oxide and a sulfide of Zr.

18. The method for manufacturing the copper alloy material according to claim 17, wherein the copper alloy containing Zr is a Cu—Zr alloy, a Cu—Zn—Zr alloy, or a Cu—Zr- or Cu—Zn—Zr-based alloy further containing at least one element selected from the group consisting of P, Mg, Al, Sn, Mn, and B.

19. A netted structure used in seawater, comprising the copper alloy material in wire or bar form as set forth in claim 2, wherein the copper alloy material is formed into a net or a grid.

20. The netted structure used in seawater according to claim 19, wherein the copper alloy material is a waved wire having curved portions, and the netted structure has a rhombically netted form made by arranging a large number of the waved wires in parallel such that the adjacent waved wires are entwined with each other at the curved portions.

21. The netted structure used in seawater according to claim 20, wherein the netted structure is configured as a fish cultivation net.

22. The netted structure used in seawater according to claim 21, wherein the fish cultivation net includes a reinforcing frame attached along the lower edge of the net in a ring-shaped manner, and the reinforcing frame maintains the shape of the lower edge of the net and applies a downward tension to the net.

23. The netted structure used in seawater according to claim 22, wherein the reinforcing frame is formed of a pipe made of the same copper alloy as the material forming the net.

24. The copper alloy material according to claim 2, wherein the phase structure has a total area ratio of the γ and δ phases of 10% or less.

25. The copper alloy material according to claim 24, wherein the Cu content [Cu] and the Sn content [Sn] satisfy the relationship $1 \leq 0.06[Cu]-[Sn] \leq 4.5$ in terms of mass %.

26. The copper alloy material according to claim 3, wherein the phase structure has a total area ratio of the γ and δ phases of 10% or less.

27. The copper alloy material according to claim 26, wherein the Cu content [Cu] and the Sn content [Sn] satisfy the relationship $1 \leq 0.06[Cu]-[Sn] \leq 4.5$ in terms of mass %.

28. The copper alloy material according to claim 4, wherein the phase structure has a total area ratio of the γ and δ phases of 10% or less.

29. The copper alloy material according to claim 28, wherein the Cu content [Cu] and the Sn content [Sn] satisfy the relationship $1 \leq 0.06[Cu]-[Sn] \leq 4.5$ in terms of mass %.

30. The copper alloy material according to claim 8, wherein the Sn content [Sn], Zr content [Zr], and P content [P] of the composition satisfy the relationships $0.5 \leq [P]/[Zr] \leq 150$, $1 \leq [Sn]/[Zr] \leq 3000$, and $0.2 \leq [Sn]/[P] \leq 250$ in terms of mass %.

31. The copper alloy material according to claim 30, wherein the phase structure has a total area ratio of the γ and δ phases of 10% or less.

32. The copper alloy material according to claim 9, wherein the Sn content [Sn], Zr content [Zr], and P content [P] of the composition satisfy the relationships $0.5 \leq [P]/[Zr] \leq 150$, $1 \leq [Sn]/[Zr] \leq 3000$, and $0.2 \leq [Sn]/[P] \leq 250$ in terms of mass %.

33. The copper alloy material according to claim 32, wherein the phase structure has a total area ratio of the γ and δ phases of 10% or less.

34. The copper alloy material according to claim 10, wherein the Sn content [Sn], Zr content [Zr], and P content [P] of the composition satisfy the relationships $0.5 \leq [P]/[Zr] \leq 150$, $1 \leq [Sn]/[Zr] \leq 3000$, and $0.2 \leq [Sn]/[P] \leq 250$ in terms of mass %.

35. The copper alloy material according to claim 34, wherein the phase structure has a total area ratio of the γ and δ phases of 10% or less.

36. The copper alloy material according to claim 8, wherein the phase structure has a total area ratio of the γ and δ phases of 10% or less.

37. The copper alloy material according to claim 9, wherein the phase structure has a total area ratio of the γ and δ phases of 10% or less.

38. The copper alloy material according to claim 10, wherein the phase structure has a total area ratio of the γ and δ phases of 10% or less.

39. The copper alloy material according to claim 11, wherein the phase structure has a total area ratio of the γ and δ phases of 10% or less.

40. The copper alloy material according to claim 36, the Cu content [Cu] and Sn content [Sn] of the composition satisfy the relationship $1 \leq 0.06[Cu]-[Sn] \leq 4.5$ in terms of mass %.

41. The copper alloy material according to claim 37, the Cu content [Cu] and Sn content [Sn] of the composition satisfy the relationship $1 \leq 0.06[Cu]-[Sn] \leq 4.5$ in terms of mass %.

42. The copper alloy material according to claim 38, the Cu content [Cu] and Sn content [Sn] of the composition satisfy the relationship $1 \leq 0.06[Cu]-[Sn] \leq 4.5$ in terms of mass %.

43. The copper alloy material according to claim 31, the Cu content [Cu] and Sn content [Sn] of the composition satisfy the relationship $1 \leq 0.06[Cu]-[Sn] \leq 4.5$ in terms of mass %.

44. The copper alloy material according to claim 33, the Cu content [Cu] and Sn content [Sn] of the composition satisfy the relationship $1 \leq 0.06[Cu]-[Sn] \leq 4.5$ in terms of mass %.

45. The copper alloy material according to claim 35, the Cu content [Cu] and Sn content [Sn] of the composition satisfy the relationship 1≦0.06[Cu]−[Sn]≦4.5 in terms of mass %.

46. The copper alloy material according to claim 39, the Cu content [Cu] and Sn content [Sn] of the composition satisfy the relationship 1≦0.06[Cu]−[Sn]≦4.5 in terms of mass %.

47. The copper alloy material according to claim 32, wherein the primary crystal in melt-solidification is in the α phase.

48. The copper alloy material according to claim 34, wherein the primary crystal in melt-solidification is in the α phase.

49. The copper alloy material according to claim 44, wherein the copper alloy material has a crystal structure whose dendrite network is fractured after melt-solidification.

50. The copper alloy material according to claim 45, wherein the two-dimensional crystal grain structure is in a circular form or a form similar to the circular form after melt-solidification.

51. The copper alloy material according to claim 49, wherein the two-dimensional crystal grain structure is in a circular form or a form similar to the circular form after melt-solidification.

52. The copper alloy material according to claim 8, wherein the composition contains an inevitable impurity being Fe, or Ni, or Fe and Ni, and the contents of inevitable impurities Fe and Ni are each 0.5 mass % or less.

53. The copper alloy material according to claim 9, wherein the composition contains an inevitable impurity being Fe, or Ni, or Fe and Ni, and the contents of inevitable impurities Fe and Ni are each 0.5 mass % or less.

54. The copper alloy material according to claim 10, wherein the composition contains an inevitable impurity being Fe, or Ni, or Fe and Ni, and the contents of inevitable impurities Fe and Ni are each 0.5 mass % or less.

55. The copper alloy material according to claim 11, wherein the composition contains an inevitable impurity being Fe, or Ni, or Fe and Ni, and the contents of inevitable impurities Fe and Ni are each 0.5 mass % or less.

56. The copper alloy material according to claim 32, wherein the composition contains an inevitable impurity being Fe, or Ni, or Fe and Ni, and the contents of inevitable impurities Fe and Ni are each 0.5 mass % or less.

57. The copper alloy material according to claim 13, wherein the composition contains an inevitable impurity being Fe, or Ni, or Fe and Ni, and the contents of inevitable impurities Fe and Ni are each 0.5 mass % or less.

58. The copper alloy material according to claim 40, wherein the composition contains an inevitable impurity being Fe, or Ni, or Fe and Ni, and the contents of inevitable impurities Fe and Ni are each 0.5 mass % or less.

59. The copper alloy material according to claim 41, wherein the composition contains an inevitable impurity being Fe, or Ni, or Fe and Ni, and the contents of inevitable impurities Fe and Ni are each 0.5 mass % or less.

60. The copper alloy material according to claim 24, wherein the copper alloy material is a plastic-processed wire or bar produced by plastic processing of a casting material.

61. The copper alloy material according to claim 28, wherein the copper alloy material is a plastic-processed wire or bar produced by plastic processing of a casting material.

62. The copper alloy material according to claim 25, wherein the copper alloy material is a plastic-processed wire or bar produced by plastic processing of a casting material.

63. The copper alloy material according to claim 29, wherein the copper alloy material is a plastic-processed wire or bar produced by plastic processing of a casting material.

64. The copper alloy material according to claim 30, wherein the copper alloy material is a cast-processed wire or bar, or a combination-processed wire or bar produced by subjecting the cast-processed wire or bar to plastic processing.

65. The copper alloy material according to claim 32, wherein the copper alloy material is a cast-processed wire or bar, or a combination-processed wire or bar produced by subjecting the cast-processed wire or bar to plastic processing.

66. The copper alloy material according to claim 34, wherein the copper alloy material is a cast-processed wire or bar, or a combination-processed wire or bar produced by subjecting the cast-processed wire or bar to plastic processing.

67. The copper alloy material according to claim 33, wherein the copper alloy material is a cast-processed wire or bar, or a combination-processed wire or bar produced by subjecting the cast-processed wire or bar to plastic processing.

68. The copper alloy material according to claim 35, wherein the copper alloy material is a cast-processed wire or bar, or a combination-processed wire or bar produced by subjecting the cast-processed wire or bar to plastic processing.

69. The copper alloy material according to claim 39, wherein the copper alloy material is a cast-processed wire or bar, or a combination-processed wire or bar produced by subjecting the cast-processed wire or bar to plastic processing.

70. The copper alloy material according to claim 43, wherein the copper alloy material is a cast-processed wire or bar, or a combination-processed wire or bar produced by subjecting the cast-processed wire or bar to plastic processing.

71. The copper alloy material according to claim 44, wherein the copper alloy material is a cast-processed wire or bar, or a combination-processed wire or bar produced by subjecting the cast-processed wire or bar to plastic processing.

72. The copper alloy material according to claim 46, wherein the copper alloy material is a cast-processed wire or bar, or a combination-processed wire or bar produced by subjecting the cast-processed wire or bar to plastic processing.

73. A method for manufacturing the copper alloy material in wire or bar form as set forth in claim 8, the method comprising a casting step in which Zr is added in a form of a copper alloy containing Zr immediately before pouring, thus preventing the addition of an oxide, or a sulfide of Zr, or an oxide and a sulfide of Zr.

74. The method for manufacturing the copper alloy material according to claim 73, wherein the copper alloy containing Zr is a Cu—Zr alloy, a Cu—Zn—Zr alloy, or a Cu—Zr- or Cu—Zn—Zr-based alloy further containing at least one element selected from the group consisting of P, Mg, Al, Sn, Mn, and B.

75. A method for manufacturing the copper alloy material in wire or bar form as set forth in claim 9, the method comprising a casting step in which Zr is added in a form of a copper alloy containing Zr immediately before pouring, thus preventing the addition of an oxide, or a sulfide of Zr, or an oxide and a sulfide of Zr.

76. The method for manufacturing the copper alloy material according to claim 75, wherein the copper alloy containing Zr is a Cu—Zr alloy, a Cu—Zn—Zr alloy, or a Cu—Zr- or Cu—Zn—Zr-based alloy further containing at least one element selected from the group consisting of P, Mg, Al, Sn, Mn, and B.

77. A method for manufacturing the copper alloy material in wire or bar form as set forth in claim 10, the method comprising a casting step in which Zr is added in a form of a copper alloy containing Zr immediately before pouring, thus preventing the addition of an oxide, or a sulfide of Zr, or an oxide and a sulfide of Zr.

78. A netted structure used in seawater, comprising the copper alloy material in wire or bar form as set forth in claim 1, wherein the copper alloy material is formed into a net or a grid.

79. A netted structure used in seawater, comprising the copper alloy material in wire or bar form as set forth in claim 3, wherein the copper alloy material is formed into a net or a grid.

80. A netted structure used in seawater, comprising the copper alloy material in wire or bar form as set forth in claim 4, wherein the copper alloy material is formed into a net or a grid.

81. A netted structure used in seawater, comprising the copper alloy material in wire or bar form as set forth in claim 6, wherein the copper alloy material is formed into a net or a grid.

82. A netted structure used in seawater, comprising the copper alloy material in wire or bar form as set forth in claim 7, the copper alloy material being formed into a net or a grid.

83. A netted structure used in seawater, comprising the copper alloy material in wire or bar form as set forth in claim 8, the copper alloy material being formed into a net or a grid.

84. A netted structure used in seawater, comprising the copper alloy material in wire or bar form as set forth in claim 9, the copper alloy material being formed into a net or a grid.

85. A netted structure used in seawater, comprising the copper alloy material in wire or bar form as set forth in claim 10, the copper alloy material being formed into a net or a grid.

86. A netted structure used in seawater, comprising the copper alloy material in wire or bar form as set forth in claim 11, the copper alloy material being formed into a net or a grid.

87. A netted structure used in seawater, comprising the copper alloy material in wire or bar form as set forth in claim 25, wherein the copper alloy material is formed into a net or a grid.

88. A netted structure used in seawater, comprising the copper alloy material in wire or bar form as set forth in claim 27, wherein the copper alloy material is formed into a net or a grid.

89. A netted structure used in seawater, comprising the copper alloy material in wire or bar form as set forth in claim 29, wherein the copper alloy material is formed into a net or a grid.

90. A netted structure used in seawater, comprising the copper alloy material in wire or bar form as set forth in claim 30, the copper alloy material being formed into a net or a grid.

91. A netted structure used in seawater, comprising the copper alloy material in wire or bar form as set forth in claim 32, the copper alloy material being formed into a net or a grid.

92. A netted structure used in seawater, comprising the copper alloy material in wire or bar form as set forth in claim 34, the copper alloy material being formed into a net or a grid.

93. A netted structure used in seawater, comprising the copper alloy material in wire or bar form as set forth in claim 15, the copper alloy material being formed into a net or a grid.

94. A netted structure used in seawater, comprising the copper alloy material in wire or bar form as set forth in claim 53, the copper alloy material being formed into a net or a grid.

95. The netted structure used in seawater according to claim 80, wherein the copper alloy material is a waved wire having curved portions, and the netted structure has a rhombically netted form made by arranging a large number of the waved wires in parallel such that the adjacent waved wires are entwined with each other at the curved portions.

96. The netted structure used in seawater according to claim 82, wherein the copper alloy material is a waved wire having curved portions, and the netted structure has a rhombically netted form made by arranging a large number of the waved wires in parallel such that the adjacent waved wires are entwined with each other at the curved portions.

97. The netted structure used in seawater according to claim 83, wherein the copper alloy material is a waved wire having curved portions, and the netted structure has a rhombically netted form made by arranging a large number of the waved wires in parallel such that the adjacent waved wires are entwined with each other at the curved portions.

98. The netted structure used in seawater according to claim 84, wherein the copper alloy material is a waved wire having curved portions, and the netted structure has a rhombically netted form made by arranging a large number of the waved wires in parallel such that the adjacent waved wires are entwined with each other at the curved portions.

99. The netted structure used in seawater according to claim 95, wherein the netted structure is configured as a fish cultivation net.

100. The netted structure used in seawater according to claim 96, wherein the netted structure is used as a fish cultivation net.

101. The netted structure used in seawater according to claim 97, wherein the netted structure is used as a fish cultivation net.

102. The netted structure used in seawater according to claim 98, wherein the netted structure is used as a fish cultivation net.

103. The netted structure used in seawater according to claim 99, wherein the fish cultivation net includes a reinforcing frame attached along the lower edge of the net in a ring-shaped manner, and the reinforcing frame maintains the shape of the lower edge of the net and applies a downward tension to the net.

104. The netted structure used in seawater according to claim 100, wherein the fish cultivation net includes a reinforcing frame attached along the lower edge of the net in a ring-shaped manner, and the reinforcing frame maintains the shape of the lower edge of the net and applies a downward tension to the net.

105. The netted structure used in seawater according to claim 101, wherein the fish cultivation net includes a reinforcing frame attached along the lower edge of the net in a ring-shaped manner, and the reinforcing frame maintains the shape of the lower edge of the net and applies a downward tension to the net.

106. The netted structure used in seawater according to claim 102, wherein the fish cultivation net includes a reinforcing frame attached along the lower edge of the net in a ring-shaped manner, and the reinforcing frame maintains the shape of the lower edge of the net and applies a downward tension to the net.

107. The netted structure used in seawater according to claim 103, wherein the reinforcing frame is formed of a pipe made of the same copper alloy as the material forming the net.

108. A copper alloy material in wire or bar form for forming a netted structure used in seawater under harsh conditions, wherein the netted structure is exposed to water or waves running at high speed and rubbing, and wherein the copper alloy material comprises a composition that does not include Mn and that does not include Ni, wherein the composition includes:
(a) 62 to 91 mass % of Cu;
(b) 0.6 to 3 mass % of Sn;
(c) one or more elements selected from the group consisting of 0.02 to 1.5 mass % of Al, and 0.02 to 1.9 mass % of Si; and
(d) the balance being Zn, wherein the composition satisfies the relationship derived from the Cu content [Cu], the Sn content [Sn], the Al content [Al], and the Si content [Si], in terms of mass %,
$62 \leq [Cu]-0.5[Sn]-3.5[Si]-1.8[Al] \leq 90$, wherein the copper alloy material has a phase structure including an α phase, a γ phase, and a δ phase, and the total area ratio of the α, γ, and δ phases is 95 to 100%, and the copper alloy material forms an Al—Sn coating or a Si—Sn coating when in seawater.

109. A copper alloy material in wire or bar form forming a netted structure used in seawater under harsh conditions, wherein the netted structure is exposed to water or waves running at high speed and rubbing, and wherein the copper alloy material comprises a composition including:
(a) 62 to 91 mass % of Cu;
(b) 0.6 to 3 mass % of Sn;
(c) one or more elements selected from the group consisting of 0.02 to 1.5 mass % of Al, and 0.02 to 1.9 mass % of Si; and
(d) the balance being Zn, wherein the composition satisfies the relationship derived from the Cu content [Cu], the Sn content [Sn], the Al content [Al], and the Si content [Si], in terms of mass %,
$62 \leq [Cu]-0.5[Sn] \leq 90$, wherein the copper alloy material has a phase structure including an α phase, a γ phase, and a δ phase, and the total area ratio of the α, γ, and δ phases is 95 to 100%, and the copper alloy material has an Al—Sn surface coating or a Si—Sn surface coating.

110. The copper alloy material according to claim 1, wherein the phase structure does not include a β phase, and the γ phase is arranged into fractured spherical fragments.

111. The copper alloy material according to claim 1, wherein the phase structure includes a β phase, and the γ phase and the β phase are arranged into fractured spherical fragments.

112. The copper alloy material according to claim 43, wherein the copper alloy material has a crystal structure whose dendrite network is fractured after melt-solidification.

113. The copper alloy material according to claim 112, wherein the two-dimensional crystal grain structure is in a circular form or a form similar to the circular form after melt-solidification.

* * * * *